(12) United States Patent
Mäkipää et al.

(10) Patent No.: US 11,725,836 B2
(45) Date of Patent: *Aug. 15, 2023

(54) ELECTRICAL FILTER STRUCTURE

(71) Applicant: Oy Lifa Air Ltd., Helsinki (FI)

(72) Inventors: Janette Mäkipää, Helsinki (FI); Vesa Mäkipää, Helsinki (FI)

(73) Assignee: Oy Lifa Air Ltd, Helsinki (FI)

( * ) Notice: Subject to any disclaimer, the term of this patent is extended or adjusted under 35 U.S.C. 154(b) by 684 days.

This patent is subject to a terminal disclaimer.

(21) Appl. No.: 16/623,794

(22) PCT Filed: Jun. 18, 2018

(86) PCT No.: PCT/FI2018/050473
§ 371 (c)(1),
(2) Date: Dec. 18, 2019

(87) PCT Pub. No.: WO2018/234632
PCT Pub. Date: Dec. 27, 2018

(65) Prior Publication Data
US 2020/0179945 A1    Jun. 11, 2020

(30) Foreign Application Priority Data
Jun. 19, 2017   (FI) .................................. 20175573

(51) Int. Cl.
*B03C 3/017*   (2006.01)
*B03C 3/019*   (2006.01)
(Continued)

(52) U.S. Cl.
CPC .......... *F24F 8/194* (2021.01); *B01D 46/0032* (2013.01); *B01D 46/0036* (2013.01);
(Continued)

(58) Field of Classification Search
CPC combination set(s) only.
See application file for complete search history.

(56) References Cited

U.S. PATENT DOCUMENTS

| 1,142,990 A | 6/1915 | Stern |
| 5,108,470 A | 4/1992 | Pick |

(Continued)

FOREIGN PATENT DOCUMENTS

| CN | 1812841 A | 8/2006 |
| CN | 2870990 Y | 2/2007 |

(Continued)

OTHER PUBLICATIONS

Cherrie et al: Effectiveness of face masks used to protect Beijing residents against particulate air pollution. Occup Environ Med, 2018, vol. 75, pp. 446-452.

(Continued)

*Primary Examiner* — Christopher P Jones
*Assistant Examiner* — Sonji Turner
(74) *Attorney, Agent, or Firm* — Laine IP Oy

(57) ABSTRACT

This publication discloses an electrostatic filter construction, to be positioned in air ducts or ventilation channels, which electrostatic filter construction includes a charging unit, which charges the particles to be filtered into a first electric potential and arranged in the filter construction in the path of the air flow before filter elements, electrically conducting electrodes connected to a second electric potential different to the potential of the charged particles and set substantially parallel to the direction of the airflow, and bag shaped filter elements positioned after the charging unit in the path of the air flow. According to the invention each bag shaped filter element has at least one designated UV-light source and an element of photo catalytic material like $TiO_2$.

33 Claims, 14 Drawing Sheets

(51) Int. Cl.

| | | |
|---|---|---|
| *B03C 3/08* | (2006.01) | |
| *B03C 3/12* | (2006.01) | |
| *B03C 3/155* | (2006.01) | |
| *B03C 3/36* | (2006.01) | |
| *B03C 3/41* | (2006.01) | |
| *B03C 3/47* | (2006.01) | |
| *B01D 46/86* | (2022.01) | |
| *B01D 46/02* | (2006.01) | |
| *B01D 46/50* | (2006.01) | |
| *B01D 46/00* | (2022.01) | |
| *B01D 53/04* | (2006.01) | |
| *B01D 53/00* | (2006.01) | |
| *B01D 53/86* | (2006.01) | |
| *F24F 8/192* | (2021.01) | |
| *B03C 3/86* | (2006.01) | |
| *F24F 8/10* | (2021.01) | |
| *F24F 8/167* | (2021.01) | |
| *F24F 8/22* | (2021.01) | |

(52) U.S. Cl.
CPC ........... *B01D 46/023* (2013.01); *B01D 46/50* (2013.01); *B01D 53/007* (2013.01); *B01D 53/0407* (2013.01); *B01D 53/8687* (2013.01); *B03C 3/017* (2013.01); *B03C 3/019* (2013.01); *B03C 3/08* (2013.01); *B03C 3/12* (2013.01); *B03C 3/155* (2013.01); *B03C 3/368* (2013.01); *B03C 3/41* (2013.01); *B03C 3/47* (2013.01); *B03C 3/86* (2013.01); *F24F 8/10* (2021.01); *F24F 8/167* (2021.01); *F24F 8/192* (2021.01); *B01D 2253/102* (2013.01); *B01D 2255/20707* (2013.01); *B01D 2255/802* (2013.01); *B01D 2257/91* (2013.01); *B01D 2259/804* (2013.01); *B01D 2279/50* (2013.01); *B03C 2201/04* (2013.01); *F24F 8/22* (2021.01)

(56) References Cited

U.S. PATENT DOCUMENTS

| | | | | |
|---|---|---|---|---|
| 5,403,383 | A | | 4/1995 | Jaisinghani |
| 5,549,735 | A | * | 8/1996 | Coppom ................. B03C 3/155 96/88 |
| 5,593,476 | A | * | 1/1997 | Coppom ................. B03C 3/155 96/88 |
| 5,993,738 | A | * | 11/1999 | Goswani .................... B03C 3/60 422/4 |
| 6,042,637 | A | * | 3/2000 | Weinberg ................ B03C 3/38 96/97 |
| 6,387,844 | B1 | * | 5/2002 | Fujishima ........... C03C 17/2456 427/430.1 |
| 6,589,489 | B2 | | 7/2003 | Morrow et al. |
| 6,632,407 | B1 | * | 10/2003 | Lau ........................ C01B 13/115 422/186 |
| 6,939,611 | B2 | * | 9/2005 | Fujishima ........... C03C 17/3417 428/689 |
| 7,160,363 | B2 | * | 1/2007 | Kulmala ................ B03C 3/155 96/84 |
| 7,309,664 | B1 | | 12/2007 | Marzolin et al. |
| 7,740,810 | B2 | * | 6/2010 | Hay ..................... B01D 53/007 422/186.04 |
| 8,263,012 | B2 | * | 9/2012 | Hay ..................... B60H 3/0608 422/186.04 |
| 9,737,895 | B2 | | 8/2017 | Genereux et al. |
| 2005/0175518 | A1 | | 8/2005 | Lin et al. |
| 2005/0223899 | A1 | | 10/2005 | Kulmala et al. |
| 2005/0238551 | A1 | | 10/2005 | Snyder et al. |
| 2007/0253860 | A1 | | 11/2007 | Schroder |
| 2008/0170971 | A1 | * | 7/2008 | Bergeron ................... A61L 9/22 422/186.04 |
| 2009/0010801 | A1 | * | 1/2009 | Murphy ................. B01D 46/10 422/4 |
| 2011/0072770 | A1 | | 3/2011 | Lakdawala et al. |
| 2012/0093691 | A1 | | 4/2012 | Mole |
| 2012/0207647 | A1 | | 8/2012 | Kim |
| 2013/0074690 | A1 | | 3/2013 | Tomimatsu et al. |
| 2015/0224218 | A1 | | 8/2015 | Burnett |
| 2015/0290478 | A1 | | 10/2015 | Curran |
| 2017/0080373 | A1 | | 3/2017 | Engelhard |
| 2017/0106218 | A1 | | 4/2017 | Lin et al. |
| 2017/0120182 | A1 | | 5/2017 | Kim |

FOREIGN PATENT DOCUMENTS

| | | |
|---|---|---|
| CN | 202569888 U | 12/2012 |
| CN | 203140156 U | 8/2013 |
| CN | 104197410 A | 12/2014 |
| CN | 106552469 A | 4/2017 |
| CN | 106622662 A | 5/2017 |
| CN | 106765658 A | 5/2017 |
| CN | 206884671 U | 1/2018 |
| EP | 1492622 B1 | 7/2014 |
| JP | 2016002545 A | 1/2016 |
| KR | 20150142971 A | 12/2015 |
| WO | WO9822222 A1 | 5/1998 |
| WO | WO0220162 A2 | 3/2002 |
| WO | WO02073094 A1 | 9/2002 |
| WO | WO03084665 A1 | 10/2003 |
| WO | WO2005014053 A2 | 2/2005 |
| WO | WO2007070704 A2 | 6/2007 |

OTHER PUBLICATIONS

Yao: Principle, design and application of air purification. China Science and Technology Press, Sep. 30, 2014.

* cited by examiner

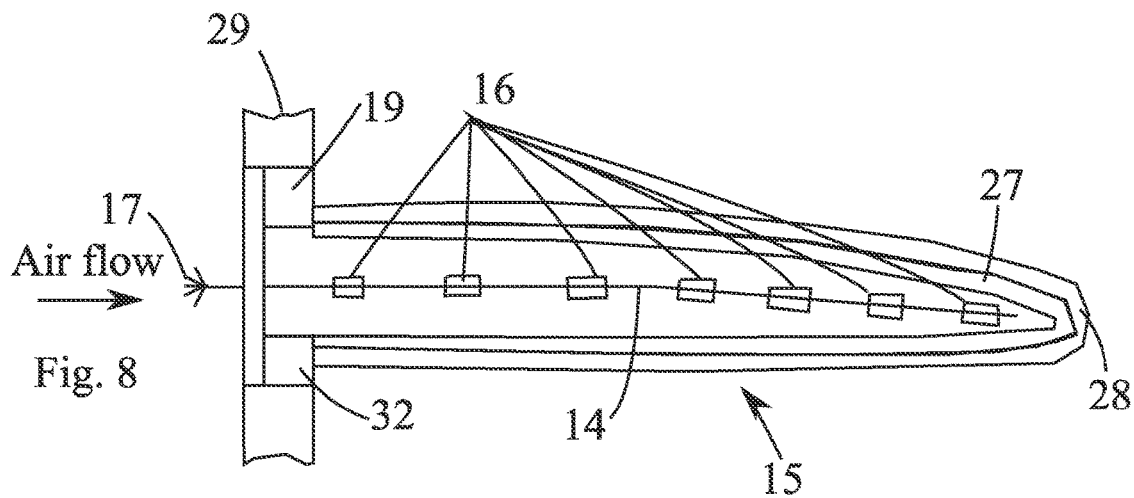
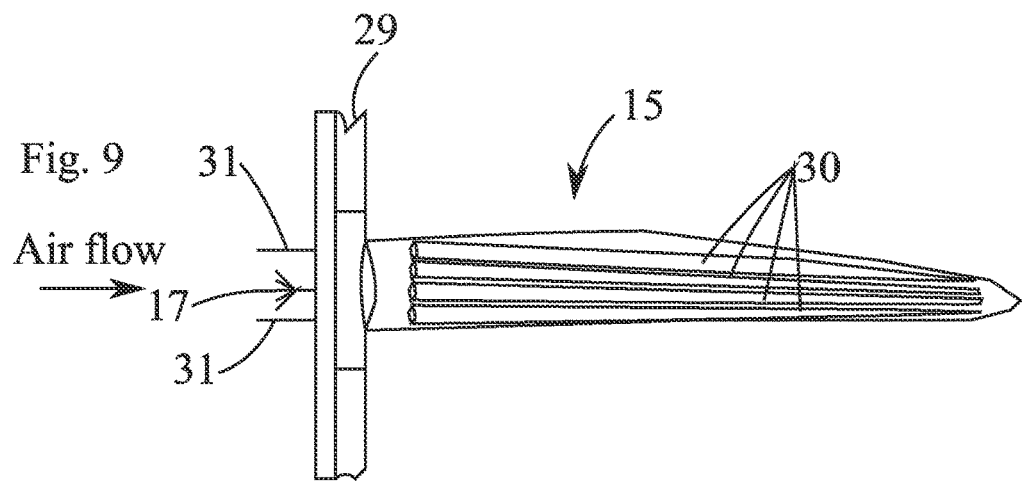
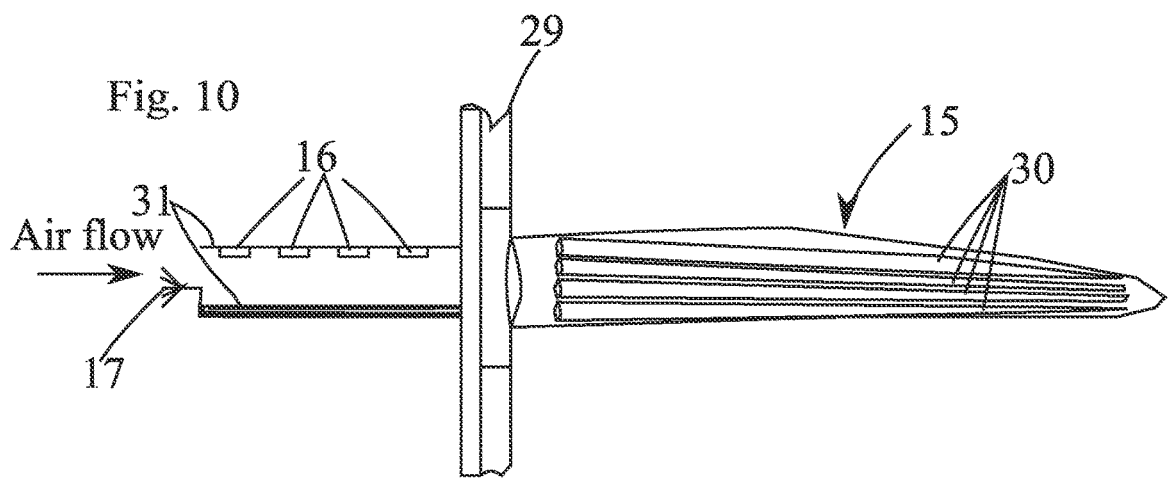

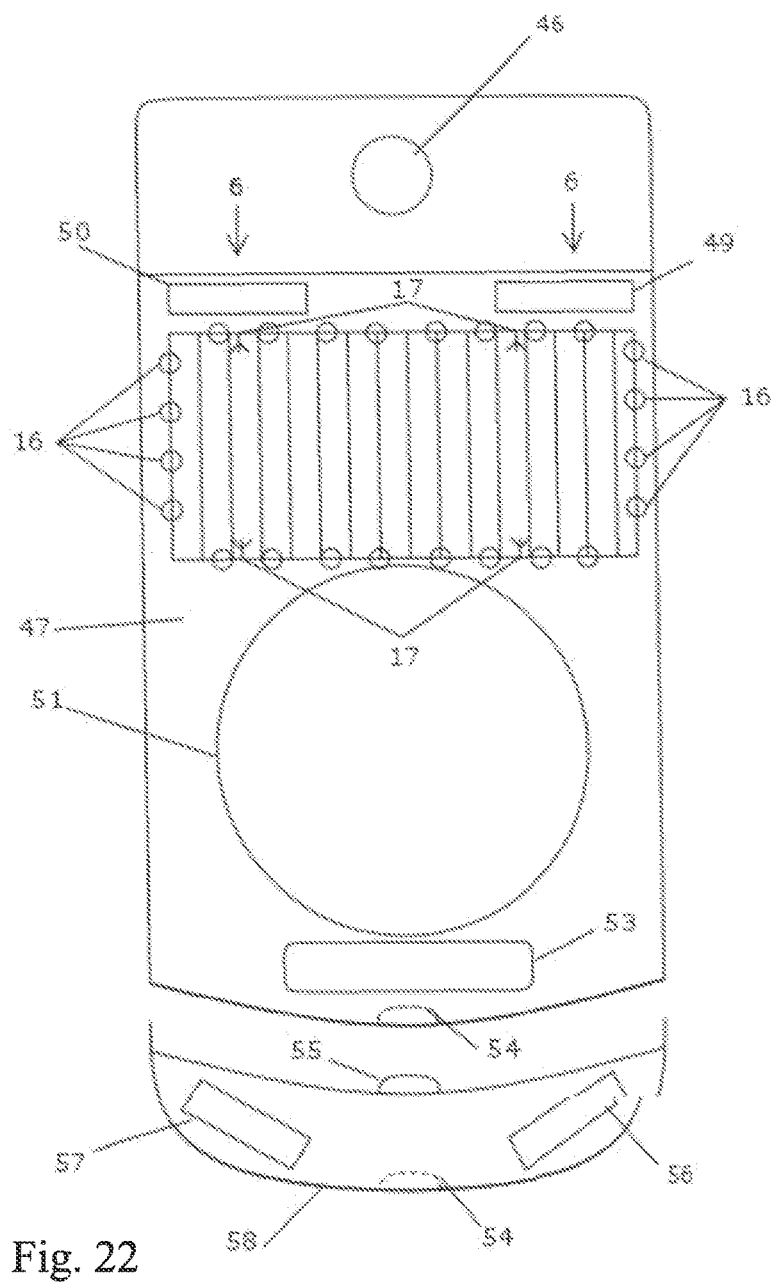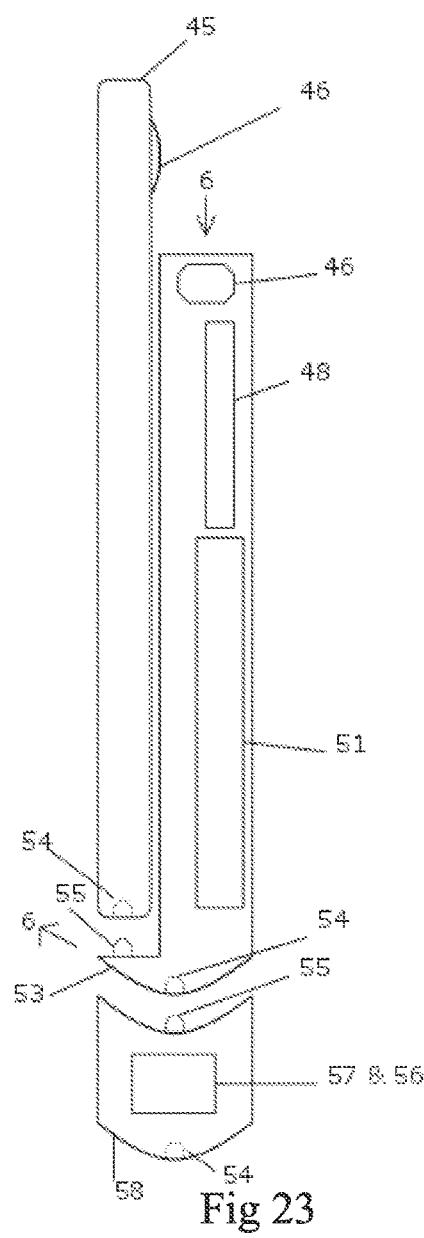
Fig. 22
Fig 23

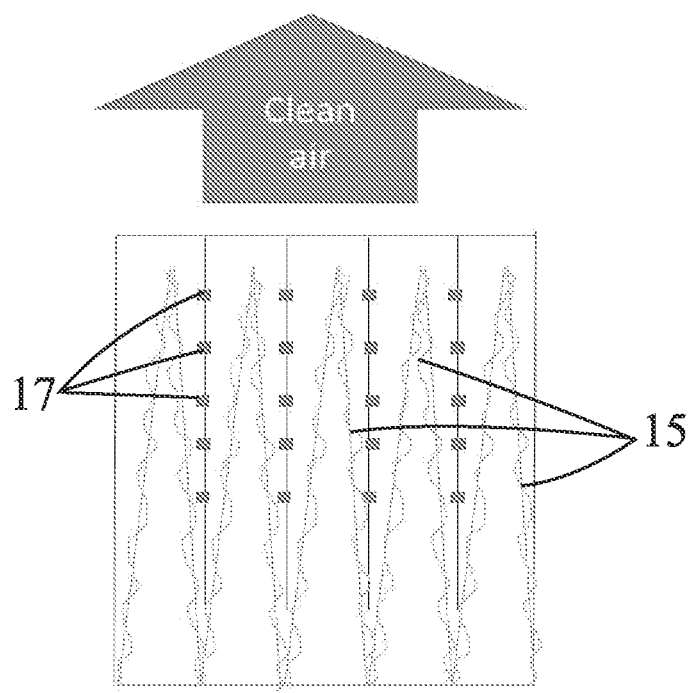
Fig. 26
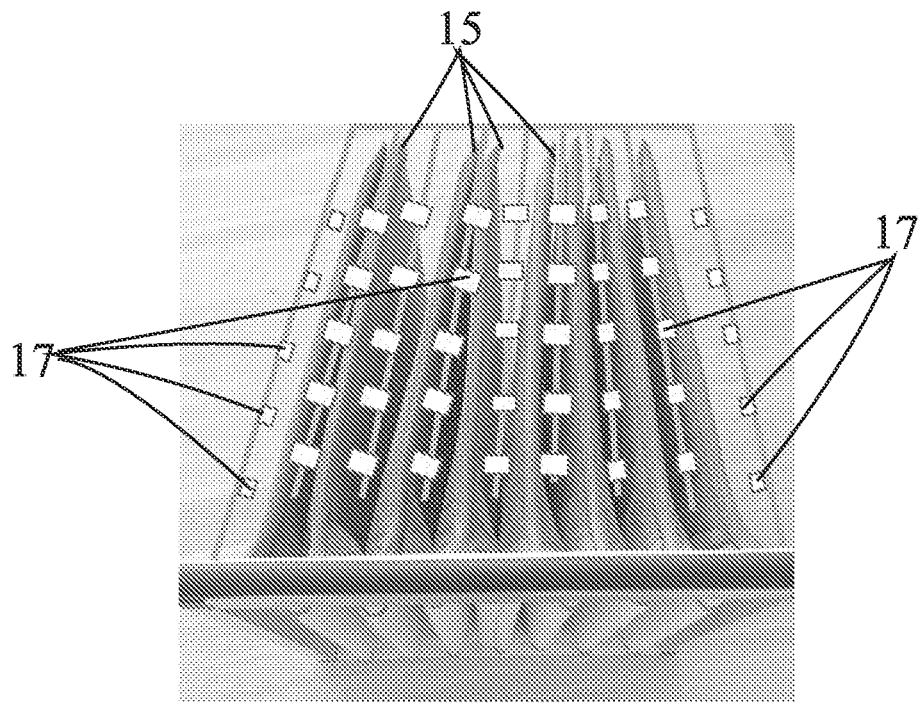
Fig. 27

ELECTRICAL FILTER STRUCTURE

The present invention relates to an electrostatic filter construction including gas and particle filters according to the preamble of claim 1.

Consciousness of air impurities and the health hazards caused by them has increased considerably in recent years. Research has shown that gaseous and particulate impurities are environmental exposure agents that clearly increase sickness and health hazards. The problems are worst in large cities, in which emissions from traffic and energy production pollute the air. Besides their health hazards, impurities in outdoor air also affect the corrosion and oxidation of materials.

Attempts are made to reduce the impurities travelling from outside to the indoor air of buildings and vehicles by filtering the incoming air. Nowadays, the replacement air for dwellings, offices, and commercial buildings is cleaned mainly using only particle filters; gases are filtered mainly only in special cases (e.g., clean rooms, electrical and electronics rooms).

The separation ability of particle filters varies greatly depending of the size of the particles. Fibre filters separate particles well if they are more than 5 µm, such as, for example, pollens. However, most of the emissions from traffic and energy production are small particles (particle size less than 1 µm), which are much more difficult to filter.

One effective way to filter small particles is the electrostatic precipitator shown in FIG. 1, the operation of which is based on an electrically charged particle and the force exerted by an electrical field on the particle. In conventional two-stage electrostatic precipitators used in air-conditioning applications, the airflow and the particles in it are first led through a charger section 1, in which they are charged electrically. The figure shows the corona wires 4 and the path 3 of the ions. After this, the airflow travels to a collector section 2, which is formed of alternating collector 9 and high-voltage electrodes 15, according to FIG. 1. The figure shows the path of a positively charged particle 5 from the filter. The corona voltage value is typically +8 kV and the collector plate value +4 kV. The distance between the plates is typically in the order of 5 mm, so that a normally sized cell contains about 100 plates. Drawbacks with an electrostatic precipitator are the complexity of the solution and its subsequent expensiveness. At the same time, the dust collecting on the collector plates can cause spark-overs, which lead to the production of unhealthy ozone, an unpleasant sound, and a temporary weakening of the filtering efficiency.

According to FIG. 2, electrostatic precipitation can also be applied to a fibre filter. The particles are charge in the same way as in the electrostatic precipitator, but the collection section 2 is formed of a fibre filter 7, above which a power electrical field is arranged with the aid of a metal mesh 7. This solution too does not eliminate the ozone production problem. The metal mesh 7 has no filtering properties.

Recently, combination filters have appeared on the market, which filter gases and particles. However, the small-particle separation efficiency of combination filters is quite modest. They generally belong to the fine filter class (F5-F9) 10 µm>Dp>1 µm in EN779 standard, which means, for example, that they filter a half or less of the 0,3-µm particles). The ability of the filters to charge gases is very modest in relation to the nominal airflow. U.S. Pat. No. 5,108,470 (Charging element having odour and gas absorbing properties for an electrostatic air filter) discloses a filter, in which a flat electrode containing activated carbon is located between two filter structures. The activated-carbon electrode is connected to an electrical power circuit. The construction is surrounded by metal electrodes, which have no filtering properties. The filter construction is at right angles to the direction of flow.

Application WO 98/22222 (Device in connection with an electrostatic filter) in turn discloses placing a fibre filter between two or more activated-carbon electrodes. In this case, the direction of the flow is parallel to the electrodes.

A general problem with flat-plate filter solutions is the small amount of gas filtering material: for the filter to be able to effectively separate gaseous impurities, the transit time through the filter material should be sufficiently long. The small amount of adsorptive material means that the charging capacity of the solutions described for gaseous impurities remains low. For this reason, the filters have a short service life. By adding consecutive filtering stages, the gas filtering ability of the alternatives referred to above can be increased, but at the same time the pressure drop will increase.

The capacity of a gas filter can be increased by using a corrugated construction, as disclosed in U.S. Pat. No. 5,549,735 (Electrostatic fibrous filter). The patent discloses a solution, in which there is a charger section, a high-voltage electrode with the same polarity as the charger section, and an earthed activated carbon electrode. The high voltage is used to form an electrical field between the metal mesh and the activated carbon electrode.

The metal mesh does not have filtering properties. It is difficult to make an even electrical field, because close to the tops of the corrugations the distance of the electrodes easily differs from what it is in the flat section. When making the creases, the upper and lower parts of the corrugations must be sealed. In addition, the parts must be impermeable to air, because the upper and lower parts do not participate in filtering.

To produce clean incoming air, a filter must be able to filter not only small particles, but also gaseous impurities. One problem is the pressure drop over the filter: present solutions cannot provide effective particle and gas filtering simultaneously with a low pressure drop. Effective filtering is also expensive to implement. In practice, this means that existing air-conditioning machinery would require more powerful and also noisier fans, in order to compensate for the pressure drop caused by the additional filtering. An increasing pressure drop over the filter will require a corresponding increase in fan energy, thus correspondingly increasing the power consumption of the fans.

WO0220162 and U.S. Pat. No. 5,403,383 describe other prior art electrical filters.

EP 03712196 describes an electrostatic filter structure with bag like filters for filtering both gases and particles.

FIG. 3 shows a solution according to EP 03712196. In the filter, electrical forces are exploited by charging the particles with the aid of a corona discharge produced, for example, using corona wires 4, and collected with the aid of an electrical field in a collector unit 2. In the charger unit 10 and the collector unit 2, voltages of the order of 8-10 kV can be used. With the aid of the electrical forces, effective filtering can be achieved for small particles too, without high pressure drops.

In this solution both electrodes 14 and 15 are manufactured from activated carbon, or some other material containing a substance that filters gases, and which has a low electrical conductivity. In this case, a material with a low electrical conductivity refers to a material with a surface resistance in the order of $10^9$-$10^{15}$ Ohms.

In order to bring the electrical filtering effect to a sufficient level, there should be a high difference in voltage potential between the electrodes 14 and 15. This can be implemented in two ways, but in practice a simple construction is one in which the electrode 14 is connected to a high voltage and the electrode 15 is earthed according to FIG. 3. This electrode can also be left floating, though this may weaken the filtering effect.

Also photo catalytic filter structures are known. However in these solutions because of free air flow with high air speed, energy dosage will be not enough to enable to destroy DNA structure of living organism inside ventilation systems. Alternatively if such arrangement will be installed inside air handling unit both initial investment and running costs are very high.

Most of the UV-lights used for HVAC industry are Mercury Lamp types (Hg, Hg—Fe, and Hg—Ga) having high radiation efficiency with high energy consumption. In addition, mercury lamps are very bad for the environment.

Based on done measurements bag filter with 300 mm deep pocket have following UVC-light density:

$$1{,}000 \mu W/cm^2 = 1{,}000 \ mW/cm^2 \text{ or } 10W/m2$$

9 cm from UV-light inside filter bag pocket, density was 650 $\mu W/cm^2$
18 cm from UV-light inside filter bag pocket, density was 400 $\mu W/cm^2$ Filters used inside Air Handling Units are normally 600 mm deep, often having several bends, thus density will be in several areas, at least in the bottom part of the pocket $0 \mu W/cm^2$.

Similarly when using UVA- and/or UVB-lights and $TiO_2$ or similar catalyst on inner filter surface inside of bag filter pockets, energy dosage needed for photocatalytic reaction cannot be reached caused by poor achievability of radiation.

The invention is to create an entirely new type of gas and particle filter. With the invention at least part of the drawbacks of the prior art referred to above can be eliminated.

The invention is based on the fact that with bag like filters the electrodes which are positioned substantially parallel to the direction of flow of the gas are equipped with ultraviolet light sources and covered with photo catalytic material like $TiO_2$. In some advantageous solutions brush like elements are used in the charging unit.

This invention is also based on fact that photo catalytic reaction will materialize only when air is in contact with photo catalytic material, that has needed energy dosage of the ultraviolet light radiation. In this invention air is forced to contact $TiO_2$ or other catalyst covered electrodes by using opposite polarity than high voltage unit ionizing the air before it.

More specifically, the particle filter according to the invention is characterized by what is stated in the characterizing portion of claim 1.

Considerable advantages are gained with the aid of the invention.

With the aid of this invention, air (or some other gas) is cleaned effectively of both gaseous and particulate impurities and with photo catalytic reaction the contaminations of the air can be decomposed and the filter bags can be sterilized. With the bag like filters and longitudinal electrodes and light sources the photo catalytic effect can be prolonged to the maximum. The construction also permits a solution with a low pressure drop. For this reason, the filter can be installed in existing ventilation systems, without changes being required in the fans. Filter bags can also be installed in every direction without the risks of bending bags. In addition to having low operating costs, the solution is also economical to implement.

When connected to existing fans in HVAC system or air purifiers, (e.g. mobile communication devices as in this invention) the filtration system can be used automatically with sensors that monitor and adjust the functions. Fans are equipped with automatic speed control that accelerates the fan according to increased power consumption, which is caused by increased pressure drop due to dust loading of filter. The calculation of increased energy consumption can be utilized to determine when the filter should be changed. This calculation can be also used to increase output current in high voltage unit(s) for ionizing and in electrodes to ensure sufficient filtration efficiency through the whole lifespan of the consumable filters.

When air purifiers (e.g. mobile communication devices in this invention) are equipped with $CO_2$ sensors, carbon dioxide levels can adjust the speed of fan automatically. These units are designated to be close enough users face for enabling clean breathing zone. The $CO_2$ sensor can detect elevated $CO_2$ level and fan will operate faster. When $CO_2$ level is low, air purifier goes to standby mode in order to save energy.

The benefits of the solutions are:
effective combined gas and particle filtering,
a long service life, if used as a filter for individual rooms,
a low pressure drop and thus low energy costs,
control of the production of the deleterious ozone that appears in electrostatic filters: the gas filter removes the ozone that arises in the corona discharge,
elimination of the need for filter-cell cleaning that arises in electrostatic filters: dirtied filters are changed frequently,
manufacture of the construction is simple and economical,
the used replaceable component can be manufactured from materials that can be disposed of by e.g. burning,
the fibre filter also acts as the insulating material for the electrodes.
electrodes can be filters
invention in mobile communication units can be used by billions of users and it will create personal clean breathing zone, wherever they are.

This invention can be used in Air Handling Units (AHU), in supply and exhaust air ventilation, in fresh air ventilation and in air purifiers.

When invention is used for cleaning the air in exhausted air in kitchen hoods and/or exhaust ducts, it can keep kitchen exhaust ventilation system clean. Invention will increase fire safety, enhance occupational safety, save energy and increase employee and customer satisfaction within commercial kitchens but it can be used in domestic purposes too. The use of invention will significantly diminish the need for kitchen exhaust cleaning, which will improve occupational safety, make the cleaning process more comfortable, cheaper and safer. As the ducts will remain cleaner, fire safety is also improved, which creates a better and safer work environment.

There are several parties that are benefiting results of the new innovation. All citizens in urban area will get rid of smells caused by kitchens and they will get healthy benefit thus spreading of unhealthy ozone can be avoided. Property owners will diminish risks of fire and get lower cost of fire insurance for their facilities and also cleaning costs of exhaust ducts will drop dramatically. Kitchen user, usually restaurant operator, will get benefit from very short cleaning time thus operation time of kitchen can be maximized. In many countries there are no existing, obligatory laws for cleaning kitchen exhaust systems. In naturally ventilated houses accumulation of grease and oil in exhaust duct will create pressure loss and designed exhaust air volumes cannot be reached—this leads high level of particles inside homes, causing serious health problems even deaths. Complains in residential buildings are often related with smells of cooking or tobacco smoke. Kitchen exhausting system is the main channel to vent out air from homes—and unfortunately there are normally lot of leakages in exhaust air ducts. By installing invention and replacing it within reasonable frequency, spreading of particles and smells can be avoided.

Commercial kitchen exhaust systems consist of a kitchen hood, exhaust ducts and an exhaust fan. Kitchen hoods are equipped with grease filters that are designed to capture the heat, smoke, odours, grease and grease vapours produced in the cooking process (RPPA). The filters need to be frequently cleaned and even if they are maintained well by the restaurant personnel, there will always be grease and dust that flow through the filter into the exhaust ducts. This is because the grease particles can be very small (<5 microns) and the air velocity as well as the temperature at the hood area are very high. This grease and dust accumulates inside the exhaust ducts as it cools down, forming a major fire hazard. To reduce the fire risk the grease and dust accumulations must be removed from the duct. This is not a simple task. Grease duct cleaning must be done by experts, it is time consuming, occupationally unsafe, expensive and environmentally very unsustainable. It requires the use of products such as of toxic substances, very alkali washing detergents, brushes, different bristles, water, disposable cloths, demanding personal protective equipment and so on. These are problems invention is here to solve. Instead of relying on unsafe, expensive, unsustainable methods, it will provide a product to prevent grease from ever reaching the exhaust ducts. Not only is the invention safer and cheaper than current applications, it is also an economically more sustainable application.

Invention as a grease collecting solution is to be installed into the kitchen hood and/or exhaust duct. Invention will increase fire safety, enhance occupational safety and improve the marketing value for commercial kitchens. The use of invention will remove or at least significantly diminish the need of kitchen exhaust duct cleaning while improving the fire safety in the kitchen. The invention will save energy and remove small particles, reducing odour complains and thus improve property value and client and employee satisfaction.

Currently both clients and contractors are dissatisfied of current commercial kitchen exhaust duct cleaning methods. Contractors who provide cleaning services have reported of unwillingness to engage in grease duct cleaning services as it was regarded grimy and potentially unsafe. Clients complained that cleaning companies tend to create harm to the clients' working conditions by, for example, spreading grease from exhaust ducts to the kitchen areas. As a solution, electrostatic precipitators are installed in kitchen exhaust. However, most of these are taken out of use, as this solution proved to not be practical. It was noted the units need to be cleaned too often, which is too costly and time consuming and thus distract regular kitchen operations. There are also other existing practices such as ozone treatment with UV-lights and cyclone type grease filters. With all these existing solutions end result is that exhaust ventilation system is, even after taken on use solution mention above, having accumulated amount of grease and oil thus those need to be cleaned within variable periods. As a conclusion, before this invention a cost-effective solution to prevent accumulation of oil and grease in kitchens is non-existing.

Commercial kitchens benefit from invention in many ways. It increases the wellbeing of the staff, since it improves the ventilation hygiene, by decreasing the odours. By decreasing odors client satisfaction will also rise, as more customers find the restaurant environment enjoyable, since there are no unpleasant odours. This again brings value to the kitchen, now that more customers will be coming in. Thirdly, as the odour complaints diminish, the neighbourhood value will rise, which brings up property value, benefitting the landlord.

In addition the staff don't need to be concerned of the kitchen exhaust system catching fire. It extends the kitchen hood filters cleaning frequency, which frees up time from the staff and they can spend their time and energy on doing what they do best: preparing and providing delicious meals. In addition to energy savings already mentioned, one embodiment of the invention enables exhaust ventilation system to be clean and operate efficiently leading to lower energy consumption.

The owner of the premise, usually the restaurant owner, is responsible for maintaining the kitchen exhaust system. Kitchen hood filters are usually maintained and kept clean by the restaurant personnel, but the duct and exhaust fan cleaning needs to be done by trained professionals. The current methods of cleaning make it an unwanted job full of occupational safety hazards, environmentally unfriendly substances, massive amounts of disposables as well as waste of energy, time and money. Ducts need to be inspected and cleaned at least once a year depending on the country's/state's legislation and the usage. In USA they need to be cleaned between 1 to 12 times a year. which causes several thousands in expenses for the restaurant. Toxic washing detergents are used to remove the grease, which makes it impossible to utilize the grease in for example biofuel production. With the invention the restaurants will have significantly less expenses, since the need of duct cleaning decreases due to the solution utilized in the product, which prevents the grease from getting further to the ducts, thus the customers will receive a cost efficient solution to improve their fire safety and sustainability.

In the following, the invention is examined with the aid of examples and with reference to the accompanying drawings.

FIG. 8 shows as a cross sectional view one filter element in accordance with the invention.

FIG. 9 shows as a cross sectional view another filter element.

FIG. 10 shows as a cross sectional view another filter element in accordance with the invention.

FIG. 22 shows a back view of an embodiment of the invention where the filter unit is combined with a mobile phone.

FIG. 23 shows a side view of the embodiment of FIG. 22.

FIG. 26 shows a schematic presentation of the invention, where the $TiO_2$ coating is placed outside the filter bags with UV-light sources.

FIG. 27 shows a practical embodiment of FIG. 26.

Figure 1:
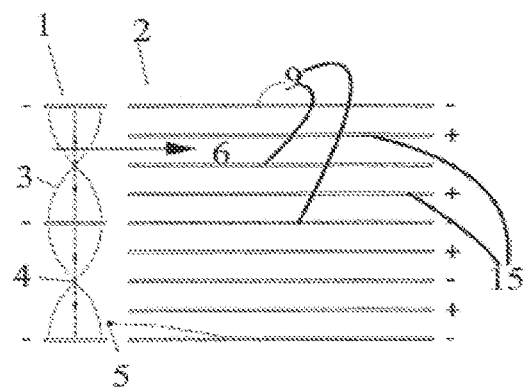
FIG. 1 shows a schematic diagram of one filter solution according to the prior art.
Figure 2:
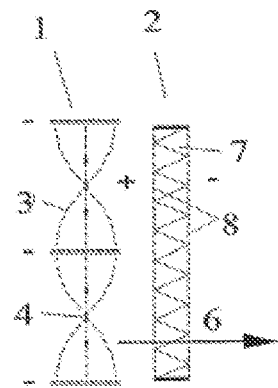
FIG. 2 shows a schematic diagram of a second filter according to the prior art.
Figure 3:
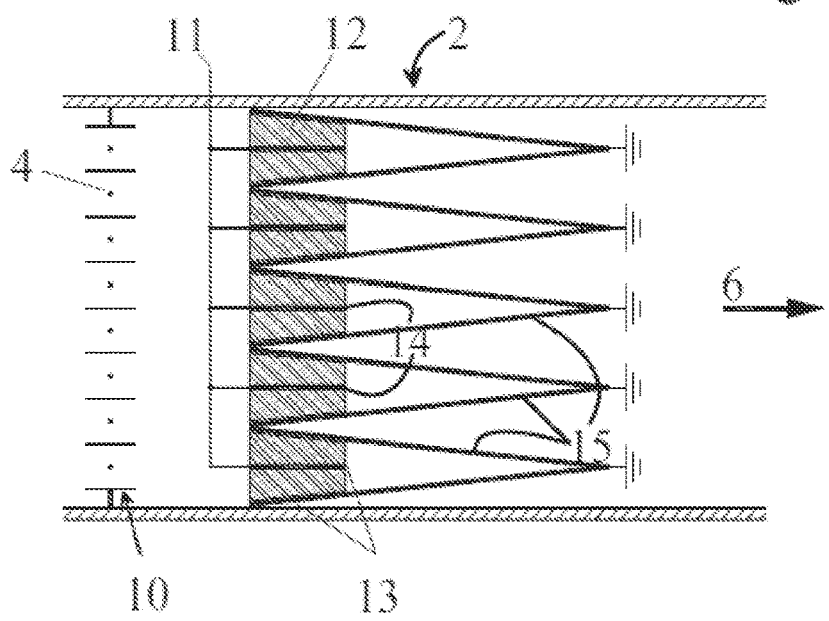
FIG. 3 shows a schematic diagram of the filter solution according to the prior art.
Figure 4:
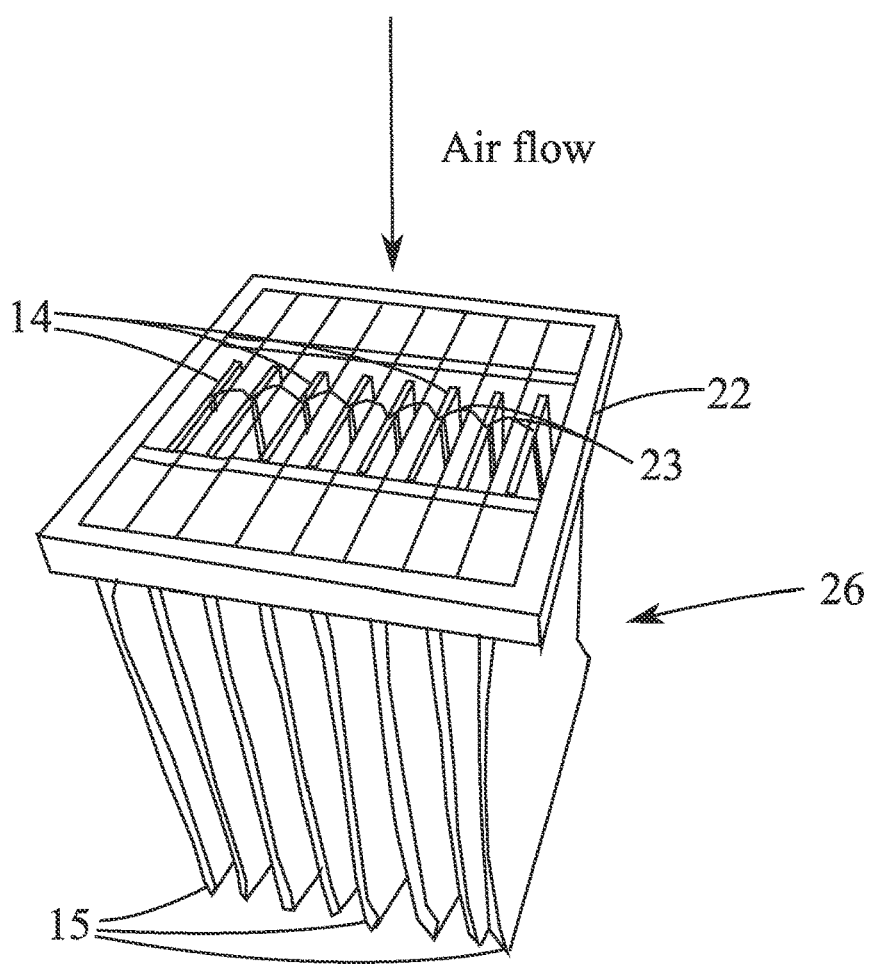
FIG. 4 shows a filter solution according to the invention.

In the following, the invention is examined with the aid of the following terms:
1 charging section
2 separation section, electrostatic filter
3 ion path
4 corona wire
5 positively charged particle
6 air flow
7 fibre filter
8 metal mesh
9 separation plate
10 charging unit
11 high voltage
12 fibre filter
13 activated carbon filter
14 positive metal electrode of the activated carbon filter or $TiO_2$ covered electrodes
15 earthed electrode of the activated carbon filter
16 UV-light sources
17 corona brushes
18 Cover plate of the charging unit
19 High voltage unit
20 Corona strip
21 Corona strip insulators
22 Frame of the electrode unit
23 Wirings of the electrodes 14 and UV-light sources
24 Support poles for the filter bags 14
25 Electrode unit
26 Filter bag unit
27 Particle filter media
28 Gas filter media
29 Filter mounting frame
30 Sub-filters
31 Grounding
32 UV-transformer
33 Positive voltage transformer
34 Positive voltage electrodes
35 Input for positive voltage
36 Protective grid in AHU solution
37 High voltage sockets
38 Corrugated filter media
39 Contactor for grounding
40 Contact for high voltage
41 Contact for high voltage
42 Fixed mounting rail
43 Adjustable mounting rail
44 Charging unit frame
45 Mobile communication device, mobile phone
46 Camera optics
47 portable filter unit
48 Removable particle filter
49 Transformer
50 High voltage unit
51 Fan
52 Support bar
53 Outlet for the air flow
54 Plug in
55 Plug
56 Particle sensor
57 $CO_2$ sensor
58 Monitor unit
61 Connector for grounding the plates (4.) or supplying electrical current for them
62 Negative ion output, carbon fiber type or similar
63 UV-A penetrable plastic sheet
64 Conductive sheet, metal or other conductive material
65 UV-A penetrable plastic sheet (same as 3.)
66 $TiO_2$ or other Nano coating in both sides of sheets
67 UV-LED stripes mounted against plastic sheets. Protected against dust, moisture and heat
68 Connector for UV-LED power supply
69 Mechanical filter, bag filter In accordance with one preferred embodiment of the invention in FIG. 4 is presented a combined filter 26 and electrode unit 25 mounted together. In operation the structure is surrounded from all sides by a ventilation duct and air flows from top to bottom in accordance with the arrow in the figure.

Electrodes 14 are positioned parallel to the air flow and covered with a suitable photo catalytic material like $TiO_2$. The electrodes 14 are typically aluminium, also other metals or other electrically conductive material may be used. On these electrode plates are positioned UV-light sources 16 on both sides of the electrode. These light sources 16 are typically LED (Light emitting Diodes) light sources assembled on suitable substrate, in this case a longitudinal circuit board extending deep into the filter bag 15. Typically the light source elements are as long as the electrodes 14. On the other hand the electrodes 14 extend almost to the end of the filter bags 15. The ratio of the length of the electrode 14 to the length of the filter bag 15 is typically around 70%, advantageously in the range of 50-95%. Wiring 23 feeds energy to the light sources 16 and as well takes care of the grounding of the electrodes 14.

Using UV-C light LED lights are installed on both sides of electrode. The main target with UV-C radiation is to destroy DNA structure of the organic material captured to the filter media. UV-A and UV-B light can also be installed in both sides of electrodes and be mainly used for photo-catalytic oxidation.

Using UV-A and UV-B led lights can also be installed inside between electrode plates (FIGS. 24-25) that must be then transparent enabling uv-light to penetrate through plates. These plates can have either honeycomb, mesh wire or nanostructure like graphene or other nano layer type structure to enhance surface area for $TiO_2$ or other catalyst above flat plates. Only electrode plate's inner side against UV-light will not be coated with $TiO_2$, all other surfaces (Electrode plates outer side and structures integrated in it) will be coated with anatase phase or combination of anatase and rutile phase of $TiO_2$. Other catalyst can also be used. Amount of LED-light depends on the usage of the filter solution, distance to catalyst and PCO efficiency needed The efficiency of LED light is measured in lumens per watt, which refers to the total quantity of light the LED lamp produces per 1 W of energy. Efficiency=total lumen output/ total power.

These light sources 16 are typically LED (Light emitting Diodes) light sources assembled on suitable substrate, in this case a longitudinal circuit board extending deep into the filter bag 15. Typically the light source elements are slightly shorter than electrodes 14. On the other hand the electrodes 14 extend almost to the end of the filter bags 15.

In one preferred embodiment of the invention the filter bag unit 26 (without the charging unit 25) is disposable, in other words the filter bags 15 will not be cleaned but replaced by a new unit when dirty. This saves essentially maintenance time and cost.

Photo catalytic material like $TiO_2$ may also be positioned in the filter bags 15 with suitable process like with wet and dry methods. In the wet method, the nano-$TiO_2$ in anatase phase of $TiO_2$ is in liquid solution which is sprayed onto the substrate. In the dry method the anatase phase of $TiO_2$ is in powder form and then led through the substrate material. Nano-coating methods such as spraying, dipping and ultra sound treating may be used.

Figure 5:
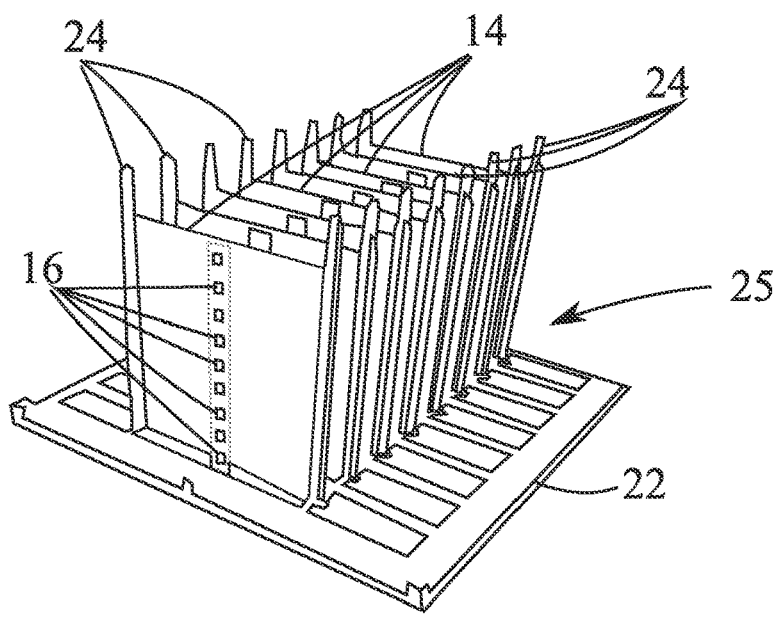
FIG. 5 shows the electrode element of FIG. 4.

First filter media to against UV-light source will be treated with photo catalyst and it can be:
non woven activated carbon filter media
electret filter material
coarse filter material
combination and or mix of the filter material named above
other filter material In FIG. 5 can be seen an electrode unit 25 turned upside down such that and UV light sources 16 are visible. The electrodes 14 are positioned between support poles 24, which keep the elastic filter bags 15 in suitable form. The frame 22 may be e.g. plastic. As can be seen from the figure one preferred embodiment includes 8 electrodes 14 and correspondingly 8 filter bags 15. Of course the number of electrode/bag pairs can vary, typically in range of 4-12.

Figure 6:
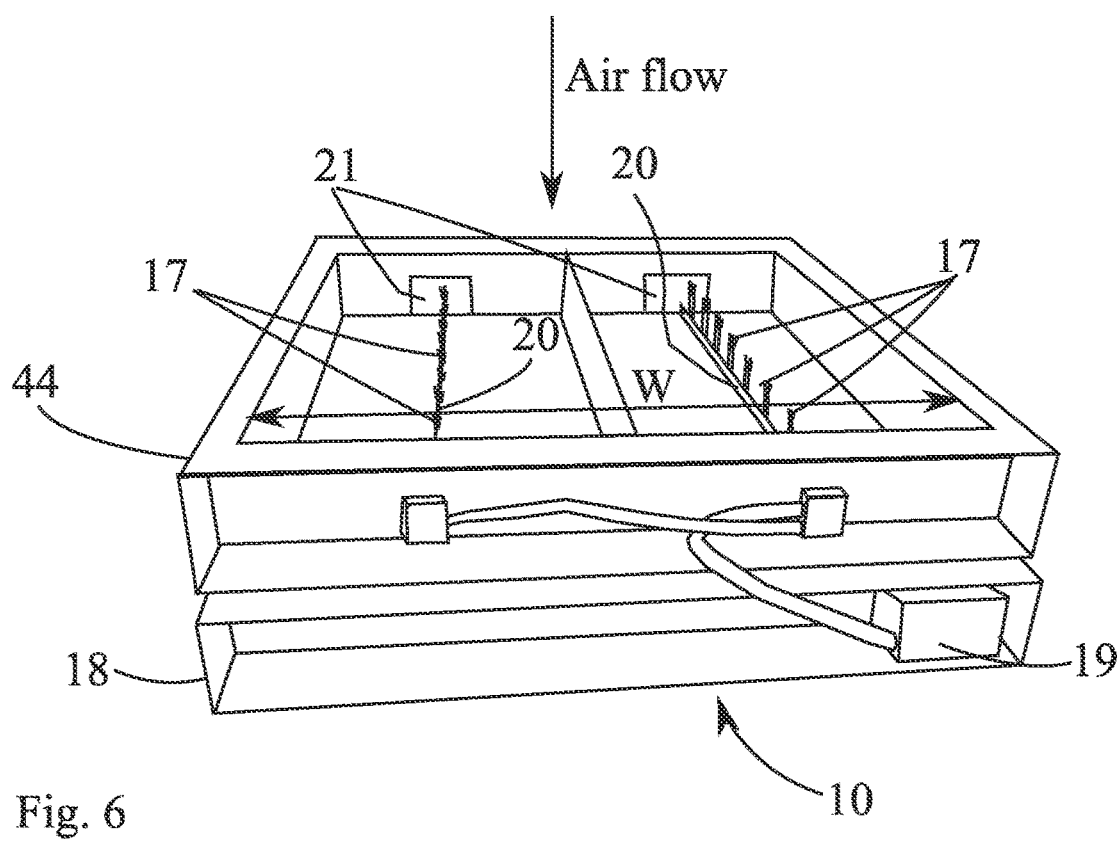
FIG. 6 shows the charging unit according to the invention.

In accordance with FIG. 6 the charging unit 10 comprises a frame 44, which is typically aluminium. Inside of the frame 44 are positioned corona strips 20 equipped with brush like extensions 17 directed against the air flow. These extensions have activated carbon fibre brushes 17 on the top. In this way the first thing high voltage item the air flow meets are these carbon fibre brushes 17. By this feature wear of the corona elements can be minimized. In this solution there are two parallel electrically conductive corona strips 20 positioned such that each strip 20 is located about 25% of the total width W away from the inside of the frame 44, where W is the total width of the inside of the frame 44. The number of corona strips 20 increases if the inner cross section (face) of charging unit 10 increases. On the other hand each brush 17 has a limited area of influence and therefore a charging unit 10 (as well as the filter structure 2) with a larger cross section (face) needs more brushes 17.

The frame 44 is typically square, also rectangle form for the frame 44 is a possible form for the frame 44. High voltage is input to the to the corona strips 20 from high voltage unit 19 of the charging unit 10. The high voltage is typically negatively charged. The corona strips 20 are insulated from the frame 44 by insulators 21. During operation cover unit 18 will be placed into the frame 44.

In operation the charging unit 10 will be placed above the construction of FIG. 4 such that the incoming air will first meet the charging unit 10 and then electrode 25 and filter bag unit 26.

Figure 7:
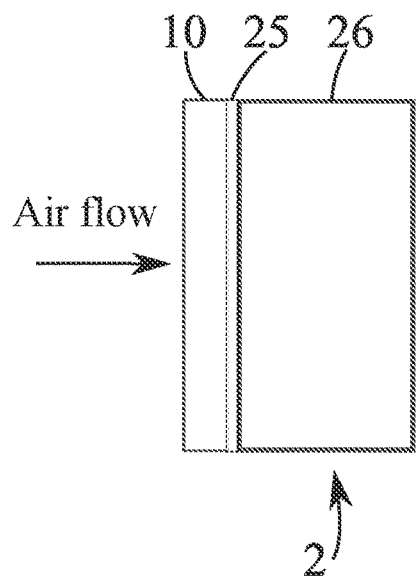
FIG. 7 shows as a block diagram one embodiment of the invention.

FIG. 7 shows an overall concept of the invention. The arrow shows tie direction of the air flow. First in the air flow is the charging unit 10, next charging unit 10 and finally bag unit 26 with filter bags.

The above described filter construction is a new effective solution to purify particle and gaseous contaminants. This invention can be used as integrated air purifier when installed in ventilation system for purifying fresh-, re-circulated or exhaust air. It can also be installed inside a casing with fan and power supply as a stand-alone air purifier. Invention can be used to replace regular filters used in Air Handling Units (AHU) having following functions: It will charge the air airflow thus enhance capturing efficiency for particles, it has photo catalytic oxidation function (PCO) as well as sterilizing ones too.

Inside filter bag's frame is installed for charging the airflow, high voltage unit (input 220-240 V, 50/60 Hz, output 12V or 24V with 6-15 kV) and for LED UV-light, electronic transformer (input 220-240 V, 50/60 Hz, output 12V).

Filter bag 15 has supporting poles 24 inside pockets where electrodes 14 (material can be varied) are positioned and are coated with a photo catalytic material like $TiO_2$ that is photo catalytically active with UV-light (here can be used, based on purpose A, B or C-UV light or combination of lights. LED UV-lights 16 are connected to the electrodes 14 such that they are close to (0.5-20 mm) to the filter media.

The filter bags 15 and electrodes 14 can be electrically connected together with connectors, thus only one electric cable connection and earth cable connection is needed to one filter bag 15/electrode 14. When installing filterbags inside AHU, existing filter frame can be used without any change only 220/240 V and earth cable need to be connected.

In advantageous embodiments of the invention the invention includes filter bags 15, charger unit 10 and a photo catalytic element with UV-light sources 16 and photo catalytic material, e.g. $TiO_2$. Further, the filter bags 15 are advantageously disposable.

In accordance with FIG. 8 in one preferred embodiment of the invention each bag filter element 15 of the bag unit 26 of FIG. 4 comprises of an aluminium electrode 14 extending to the bottom or almost to the bottom of the bag filter element 15. The electrode 14 is covered with photo catalytic material like $TiO_2$ and also has UV-light sources 16 on both sides of the electrode. Advantageously the electrode 14 is grounded to earth potential. The incoming air is charged by high negative voltage by brushes 17 fed by high voltage unit 15 and the UV-lights 16 are fed by transformer 32 with low voltage. The bag filters 15 typically comprise at least two layers namely particle filter media 27 as inner structure for capturing small impurities in particle for and a gas filter media layer 28 as an outer structure for capturing gaseous materials. The gas filter media layer may be e.g. activated carbon. The media layers 27 and 28 may be combined together e.g. by ultrasonic welding. The bag like filters 15 are mounted in a filter mounting frame 29 side by side as can be seen from FIG. 4 in order to cover the complete inner cross section (face) of the filter structure 2. In this solution the inside of bag 27 may be alternatively covered with $TiO_2$ or the $TiO_2$ cover may be in both surfaces 27 and 14.

In accordance with FIG. 9 a basic solution is presented where such a filter structure 15 is used comprising multiple sub-filters 30 inside the main filter bag. Also here the filter 15 is mounted to filter mounting frame in the same way as in FIG. 4. In the incoming air is positioned charging unit with brushes 17 and grounding elements 31 like earthed metal plates. Here the charging unit may be assembled to existing filter structures.

FIG. 10 is a modification of FIG. 9 such that each filter element 15 has a designated photo catalytic element in front of them in the air flow path in form of UV-lights 16 and grounded metal plates 31 with photo catalytic material like $TiO_2$. In addition the structure comprises charging brushes 17 isolated electrically from the grounding elements 31.

Anatase phase TiO2 band gap is 3.2 eV.

Installing LED based UV lamps are much cheaper but light density is low thus they must be installed nearby surfaces to be radiated.

This invention has very small initial investment cost and low running costs comparing the existing separate solution available in the market.

Figure 11:
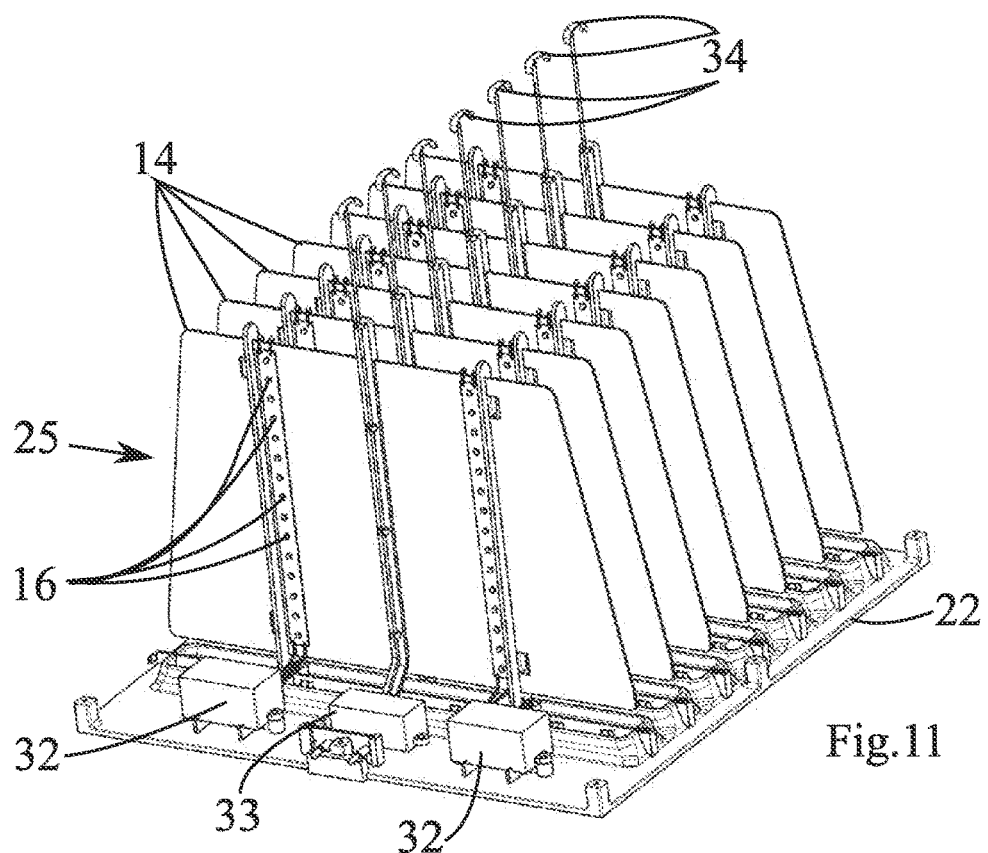
FIG. 11 shows another embodiment of the charging unit of FIG. 5.
Figure 12:
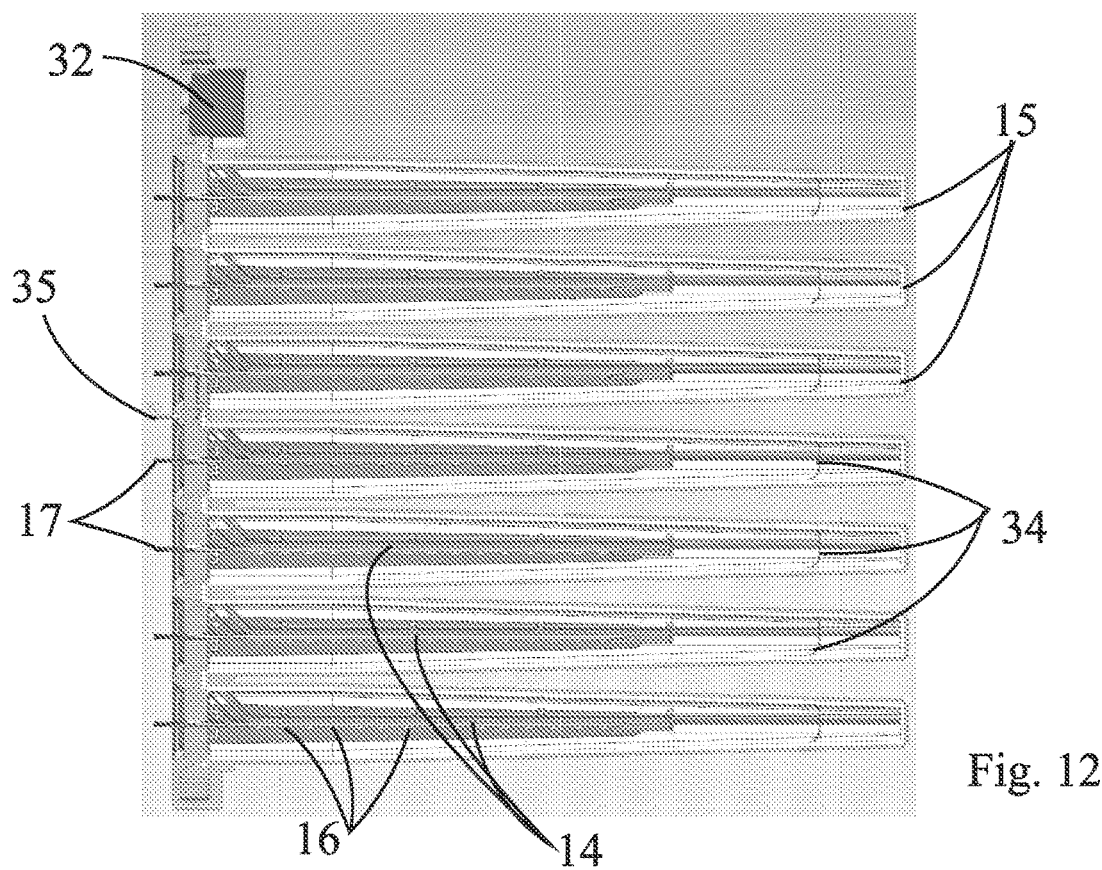
FIG. 12 shows a cross section of the charging unit of FIG. 11 positioned inside the filter bag unit in accordance with the invention.
Figure 13:
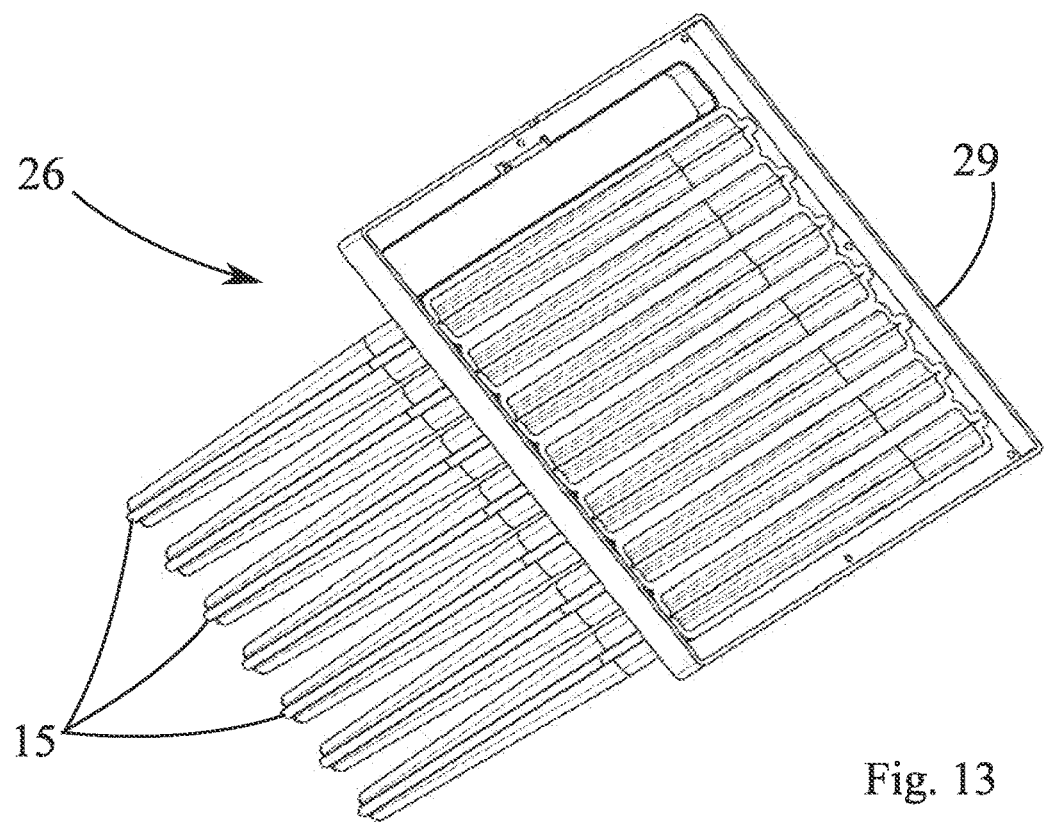
FIG. 13 shows a filter bag unit in accordance with the invention.

In FIGS. 11 and 12 are presented an embodiment where the electrode unit 25 is equipped with a positive electrode structure 34 for each of the electrodes 14 such that the tip of this electrode structure charges the insides of the filter bags 15 of FIG. 12 with positive charge of around 1 kV. The voltage depends on the material of the bag 15 as well as the mechanical properties of the tip of the electrode structure 34. These electrodes 34 are fed with a transformer 33, which gets its input from connector 35 of FIG. 12. The electrodes 14 are typically grounded and isolated from the positive electrodes 34. In FIG. 11 there are two rows of UV-light sources 16 on both sides of the electrodes 14. In accordance with the invention there could be even two additional rows of these UV-light sources 16 on both sides of the electrodes 14 positioned for example on the outer sides of the electrodes 14, in other words on the left and right sides of each electrode in FIG. 11 such that maximum area onside the filter bags 15 would be illuminated by the UV-light. These UV-light sources 16 are fed by UV-transformers 32. Also here the inside of the bag filters 15 may be covered with $TiO_2$.

As can be seen from FIG. 12 the filter bags 15 may have two bags inside each other like in FIG. 8 however the inner bag must be at least partially conductive in order to charge it with positive voltage.

Figure 14:
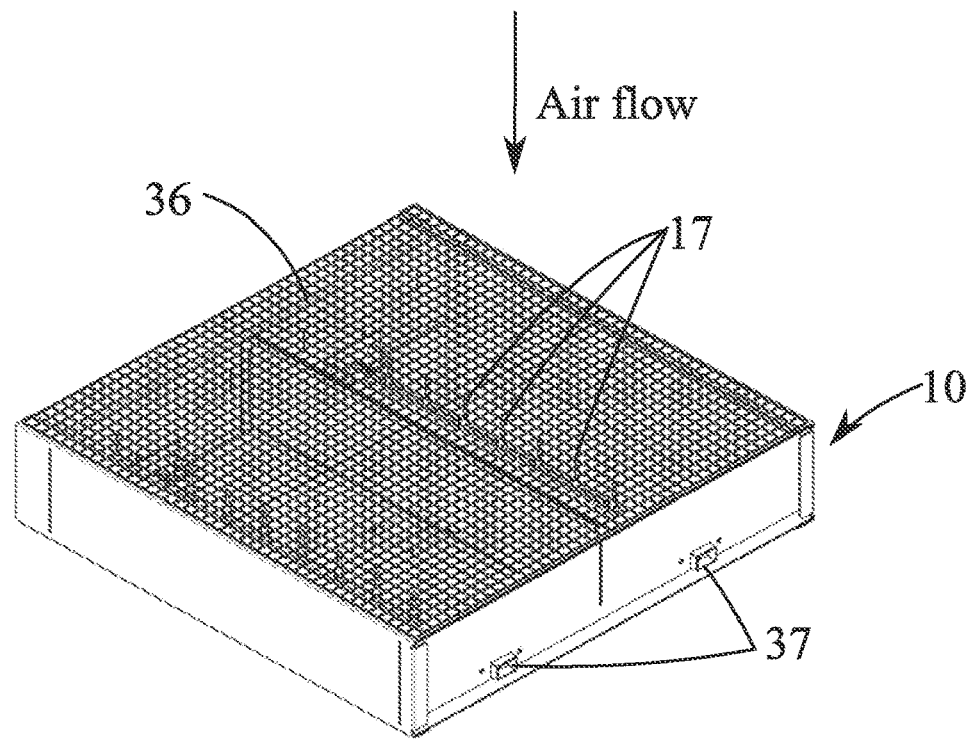
FIG. 14 shows another charging unit in accordance with the invention.

FIGS. 12 and 14 show also the corona brushes 17 for negative charging of the air flow.

The bags materials may be the following:
Inner bag 27 (FIG. 8)
  Coarse filter, typically 250-500 g/m²
Outer bag 28 (FIG. 8)
  Fine filter, typically 100-250 g/m²

The referred classifications are based on EN799 standard can be found e.g. on web page: http://apps.who.int/medicinedocs/en/d/Js14065e/12.html#Js14065e.12

Particulate matter in ISO 16890 describes a size fraction of the natural aerosol (liquid and solid particles) suspended in ambient air. The symbol ePMx describes the efficiency of an air cleaning device to particles with an optical diameter between 0.3 µm and x µm. The following particle size ranges are used in the ISO 16890 series for the listed efficiency values.

Optical particle diameter size ranges for the definition of the efficiencies, ePMx

| Efficiency | Size range, µm |
| --- | --- |
| ePM10 | $0.3 \leq x \leq 10$ |
| ePM2.5 | $0.3 \leq x \leq 2.5$ |
| ePM1 | $0.3 \leq x \leq 1$ |

These materials may be impregnated for removal/adsorption/absorption of different gases, one for $SO_2$ and the other for $NO_X$.

The inner media bag 27, which can also be the only filter bag, can be impregnated by $TiO_2$ for better photo catalytic oxidation function. It can also be impregnated against gases PCO is not effective enough. There are several alternatives for suitable combinations of substrates/impregnates. Some are non woven activated carbon filter media
  electret filter material
  coarse filter material
  combination of above mention filter materials.

Like for sulphur dioxide impregnation can be done by various methods using different impregnates like KOH and $KMnO_4$. The impregnation process can be done with wet and dry methods. In the wet method the impregnant is in water solution which is sprayed onto the substrate. In the dry method the impregnant in powder form is aerosolised and then led through the substrate material.

The capacity of the gas filter is related to the mass of impregnant deposited on the substrate material. On the other hand, the deposited impregnant increases the pressure drop of the fibrous filter, or may reduce the adsorption capacity of other gaseous impurities in case of impregnation of the non-woven activated carbon substrate. Therefore the optimum amount of impregnant depends on the impregnant/substrate combination.

By using filter bags 15 with dimension 592*592*592 mm one filter unit with 10 bags would have 7 m² filter surface. With ten 500*500 mm² electrodes 14 covered on both sides with $TiO^2$ in each filter bag 15 each filter unit would have 5 m² $TiO_2$ covered surface.

FIG. 14 shows a filter bag unit 26 without the charging unit 10. In this embodiment the corona brushes 17 are protected by a protective grid 38 in order to avoid electric shocks of maintenance personnel. The complete housing of the charging unit 10 is advantageously grounded. High voltage is fed to the corona brushes 17 through high voltage sockets 37.

Figure 15:
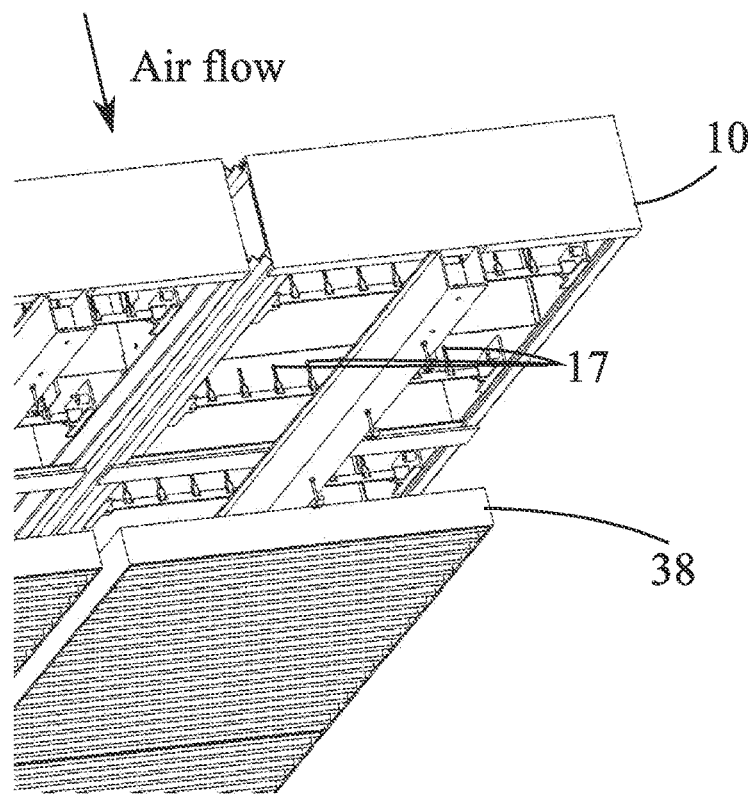
FIG. 15 shows a filter construction where several charging units of FIG. 14 are combined together and combined with a filter construction.
Figure 16:
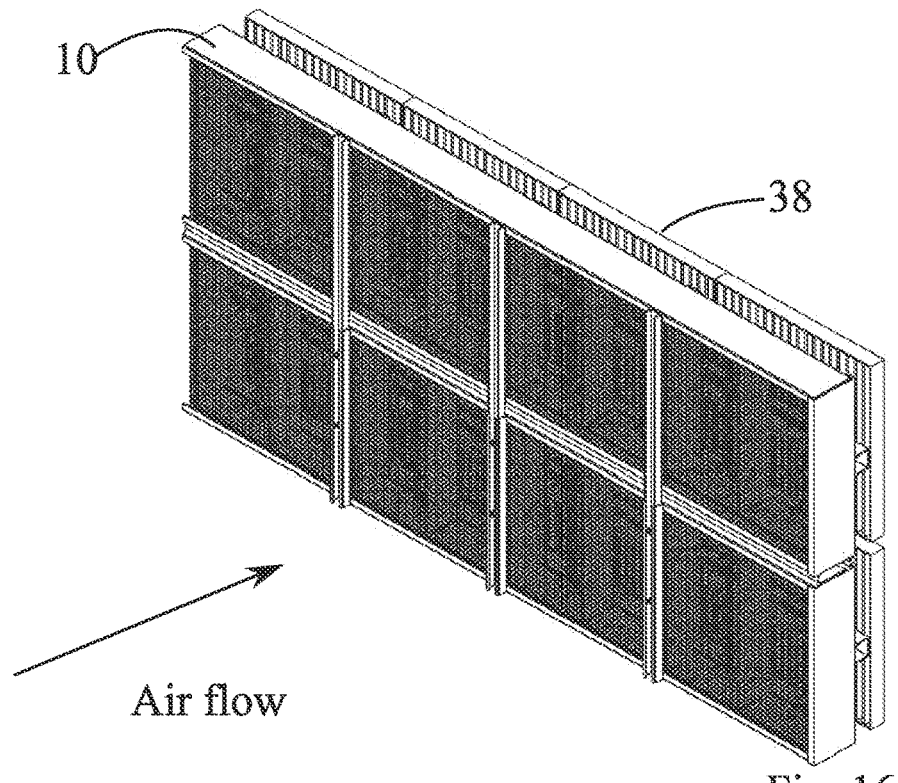
FIG. 16 shows a filter construction of FIG. 15 where the filter unit is assembled to the charging unit.

FIGS. 15 and 16 show a charging and filter unit, where several charging units 10 are combined as a wall to fit different sizes of ventilation ducts. Filter units 38 in form of corrugated filter media are positioned after the charging units including the corona brushes 17.

Figure 17:
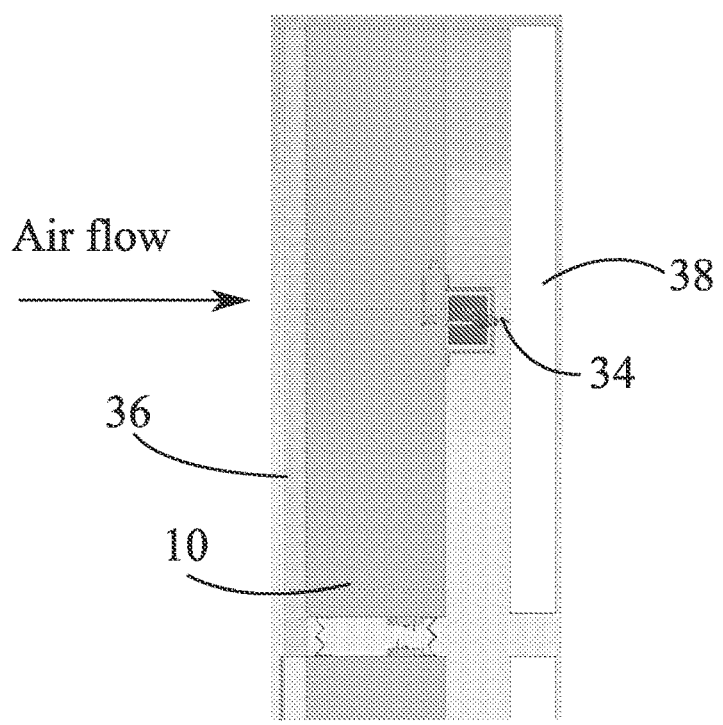
FIG. 17 shows a cross section of FIG. 16.
Figure 18:
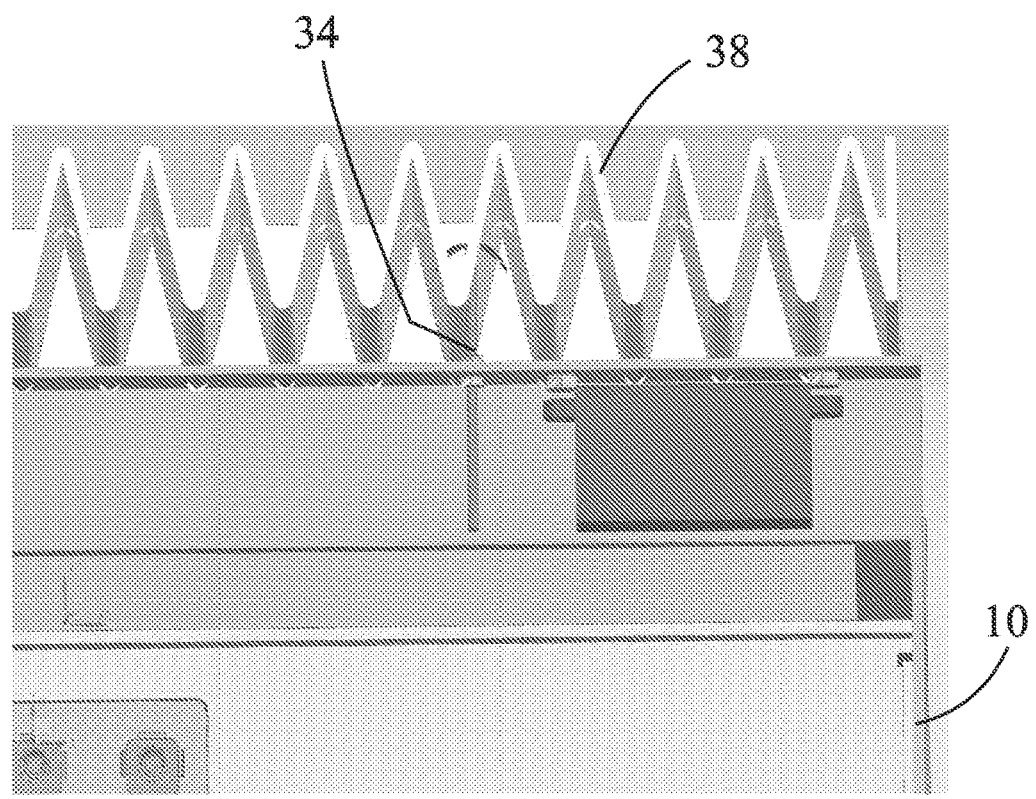
FIG. 18 shows a more detailed view of FIG. 17.

FIGS. 17 and 18 show a cross section of FIG. 16, where the air flow first meets the charging unit 10 having a protective grid 36. After the charging unit 10 in the air flow passes through a corrugated filter media 38. This media is advantageously charged with positive voltage electrodes 38 and in this case it is advantageous that the filter media 38 is at least partially conductive. The positive voltage connected to electrodes 34 varies based on material of the media but is typically in the range of 1 kV. The filter media 38 comprises advantageously two layers, namely a layer of particle filter media and of gas filter media. Further, the filter media closest to the charging unit 10 is advantageously electrically conductive either as such or combined to another layer having gas filtering properties.

Figure 19:
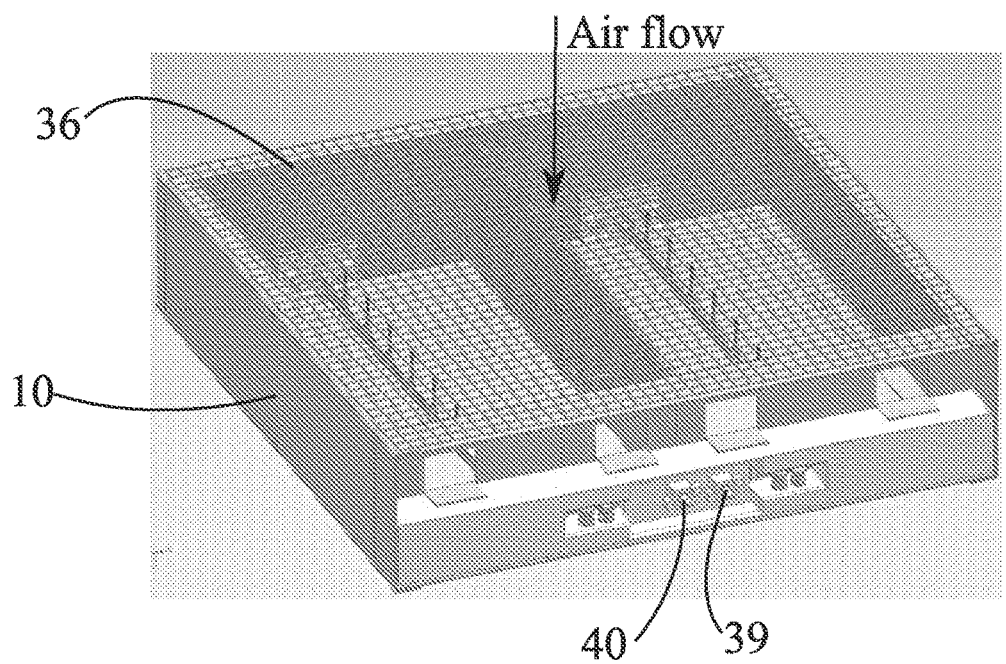
FIG. 19 shows one connectable embodiment of the charging unit to form a construction shown in FIGS. 15 and 16 in accordance with the invention.
Figure 20:
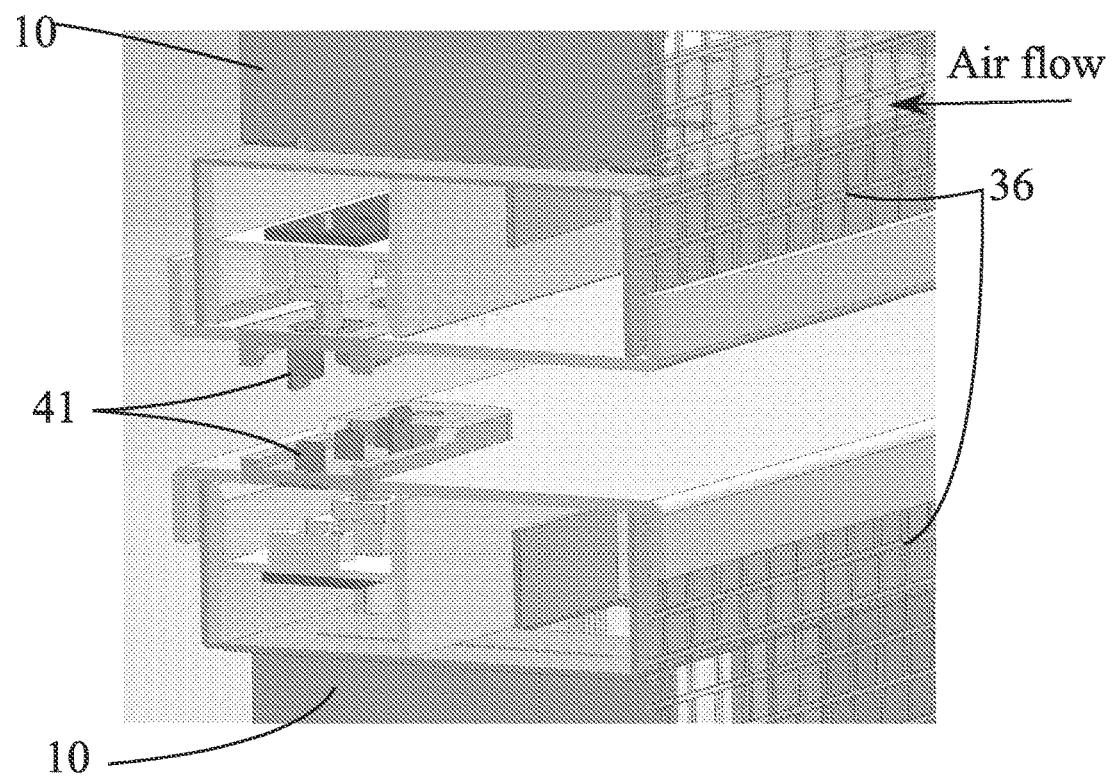
FIG. 20 shows details of the charging unit to form a construction shown in FIGS. 15 and 16 in accordance with the invention.

FIG. 19 shows one connectable embodiment of the charging unit to form a construction shown in FIGS. 15 and 16 in accordance with the invention to form a charging wall from multiple charging units 10. This is enabled by connectors for grounding 39 and negative high voltage 40 on the sides of the charging units 10 for connecting charging units next, or opposite to 10. FIG. 20 shows connectors 41 for positive voltage contacted to electrodes 34. These connectors are used as well connecting charging units next to or opposite to 25 in to each other.

Figure 21:
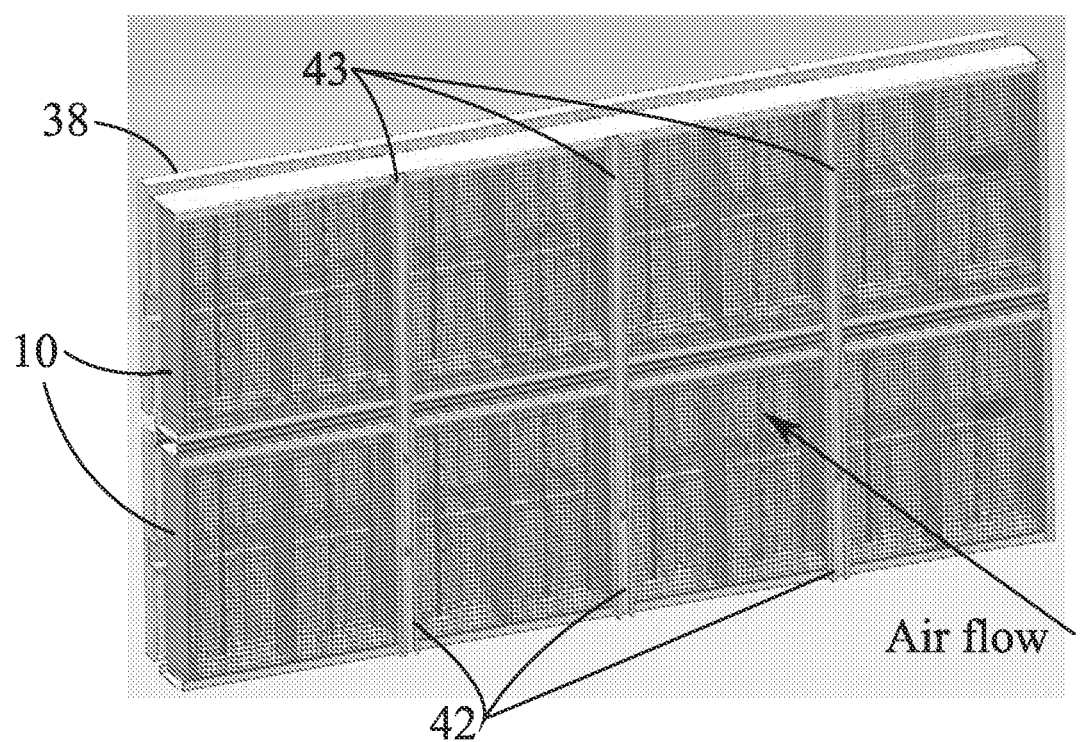
FIG. 21 shows mounting details of the charging unit to form a construction shown in FIGS. 15 and 16 in accordance with the invention.

FIG. 21 shows mounting rails 42, 43 of the invention for mounting the filtering unit to a fixed structure e.g. in front of a ventilation duct. The rails 42 are fixed to the filter structure and rails 42 slide inside the fixed rails 42 in order to make it possible to adjust the vertical position of the filter wall.

In accordance with the invention the polarities of the corona brushes 17 and positive electrodes 34 may be reversed.

In accordance with FIGS. 22 and 23 the filter unit 47 is combined with a mobile phone 45 or other mobile telecommunications device. Preferably the unit is positioned on the back side of the phone such that it does not block the camera optics 46. The inlet of the airflow 6 is on the back side of the phone 45 and the outlet preferably arranged such that it directs the air flow 6 to the face of the user. The device includes a fan 51 for producing the air flow and a high voltage unit 50 for charging the incoming air and particles preferably with help of corona brushes 17. In addition the filter comprises electrically conductive electrodes 14 covered with $TiO_2$ and preferably connected to opposite high voltage than the corona elements, preferably corona brushes 17. In addition the filter unit 47 comprises UV-light sources 16, typically LED's with corresponding transformer 49. If the voltage of the phone is suitable for the LED's the transformer may be omitted. The filter unit may also include a removable particle filter 48 and include other conductive material for filtering particle and gas contaminants. The filter unit 47 may be removable aftermarket unit or OEM part of the phone like filter phone. In addition, the unit 47 may be disposable or reusable.

Additional monitoring device 58 consists of carbon dioxide sensor 57 and/or particle sensor 56. The device is connected directly to filter units pin out 54 connector and has itself a pin 55 for further connection.

Figure 24:
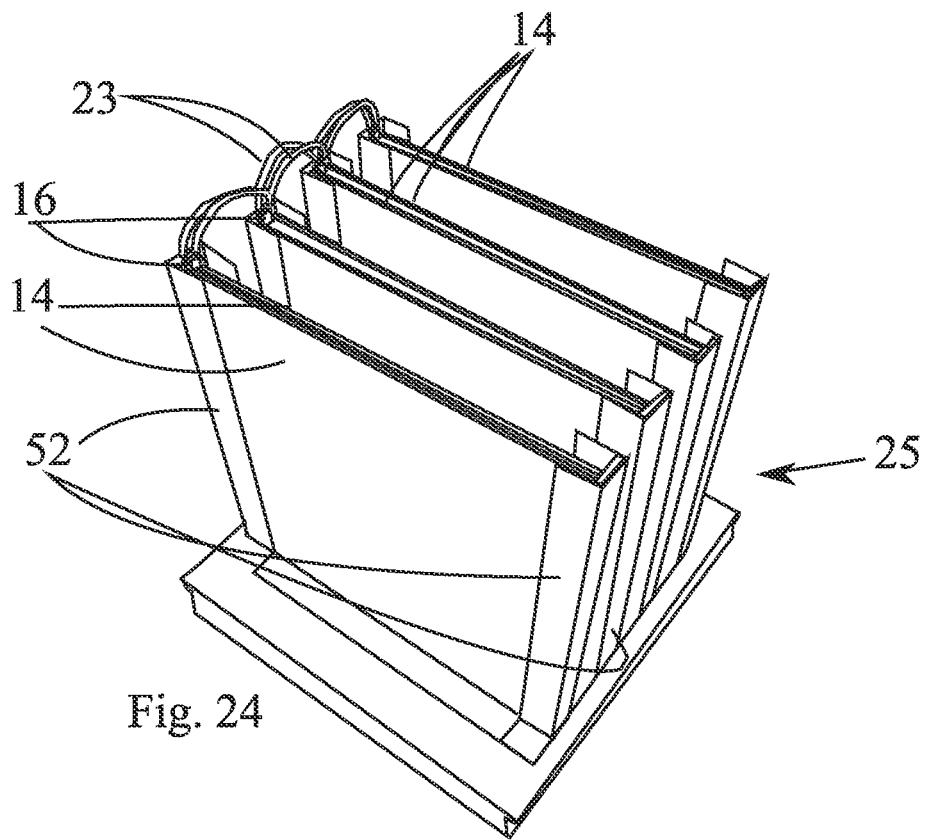
FIG. 24 shows a perspective view of an embodiment of the invention where the electrodes are formed of transparent, electrically conductive film like material.

FIG. 24 shows a perspective view of an embodiment of the invention where the electrodes 14 of the electrode unit are formed of transparent, electrically conductive film like plastic material. This plastic material is typically fixed by glue to support bars 52. Advantageously these plastic electrodes are connected to high voltage with opposite polarity than the high voltage of the charger unit. UV-leds 16 are positioned on both sides of the electrodes 14 to the support bars 52 and electrically connected with conductors 23 to supply voltage.

Figure 25:
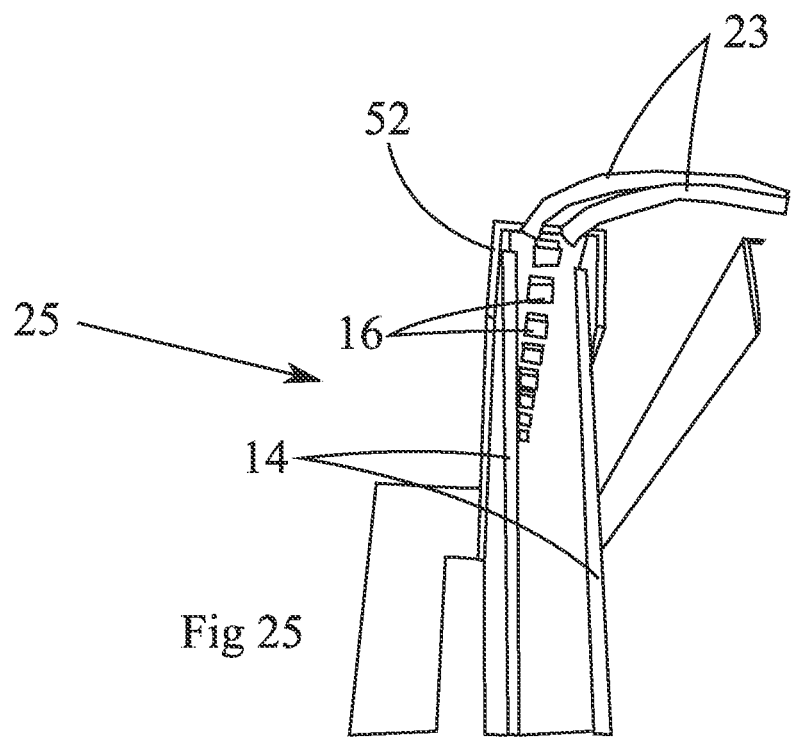
FIG. 25 shows a detail of FIG. 24.

FIG. 25 shows in more detail positioning of the LEDs inside the support bars 52, in this case support bars 52 of U-profile.

FIG. 26 shows a schematic presentation of the invention, where the $TiO_2$ coating is placed outside the filter bags with UV-light sources 17 and FIG. 27 shows a practical embodiment of FIG. 26.

Figure 28:
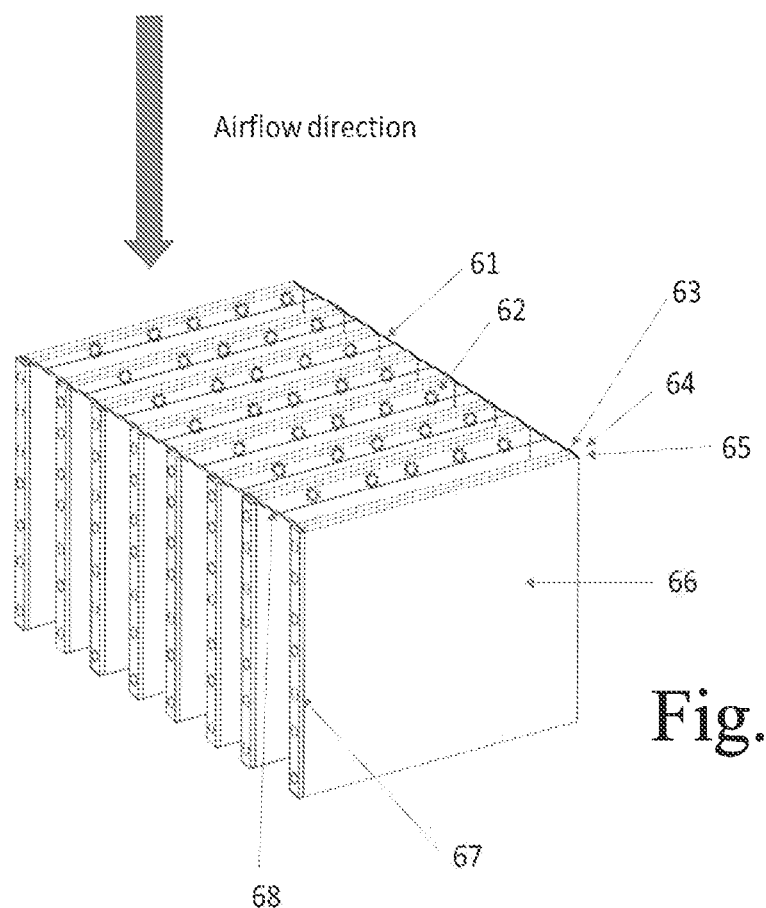
FIG. 28 shows an alternative filtration unit in accordance with the invention.

In accordance with FIG. 28 a filtration unit (PECO), may work independently or can be connected to other filtration solutions. This solution includes a connector 61 for grounding the plates 64 or supplying electrical current for them. The unit includes also a negative ion output 62, carbon fiber type or similar. One element of the unit includes UV-A penetrable plastic sheet 63 positioned in direction of the air flow aid beside it a conductive sheet 64 of metal or other conductive material. On the other side of the metal sheet 64 is located a UV-A penetrable plastic sheet 65, same type as sheet 63. $TiO_2$ or other Nano coating 66 in applied on both sides of sheets 63 and 65, possibly also on sheet 65. UV-LED stripes 67 are mounted against plastic sheets 63 and 65. The LEDs are typically protected against dust, moisture and heat. The unit includes also a connector 68 for UV-LED power supply.

This solution can be used as a stand alone filtration system (PECO). The number, width and depth of the plates can be adjusted.

Plates can be easily removed from the frame and they are also washable.

Different types of coatings, corona discharge points, LEDs and sheet materials can be used.

Figure 29:
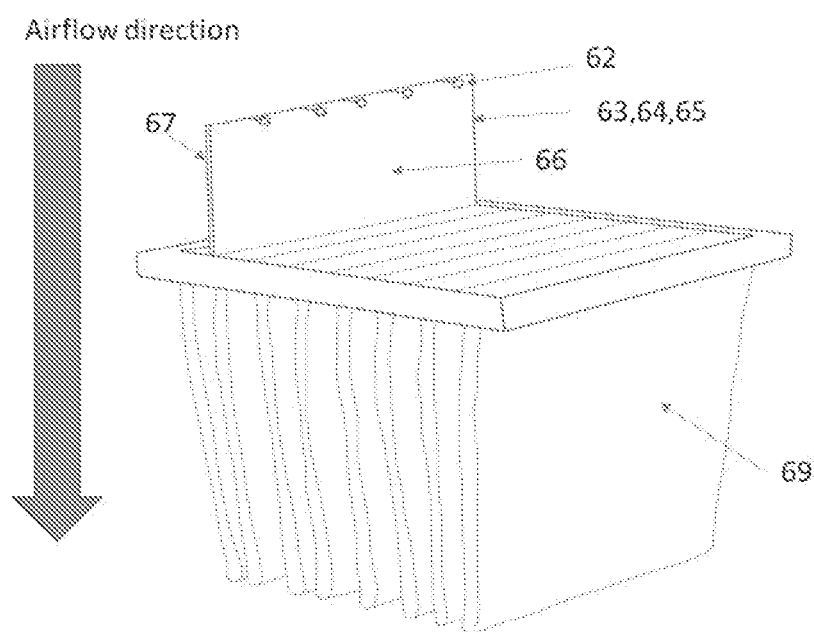
FIG. 29 shows the solution of FIG. 28 partially assembled into a bag filter.

In accordance with FIG. 29 the negative ion output 62 may be formed by carbon fiber type or similar. The structure of single elements is the same as in FIG. 28:

UV-A penetrable plastic sheets 63 and 65 on both sides of a conductive sheet 64 of metal or other conductive material. $TiO_2$ or other Nano coating is used on both sides of sheets. In addition UV-LED stripes 67 are mounted against plastic sheets 63 and 65, also protected against dust, moisture and heat. The above structure is positioned inside a mechanical filter 69, bag filter in this solution.

In FIG. 29 one filter plate is placed partially inside filter bag unit. In real application each bags would have one sandwich type filtration unit.

If the unit is completely in front of other filter unit, the amount of sheets can be customized.

The solution of FIGS. 28-29 can be fitted inside different types and shapes of filters like bag type or pleated. The UV-LEDs 67 are protected against heat and moisture, can be used in difficult conditions such as in grease ducts. The metal plates 64 in between of plastic sheets can be either grounded or connected to reverse polarity than ionizing unit 62 in front of the filter. This filtration unit can be lowered in to same level as mechanical filter or be extended to be at least partially in front of it.

Instead of $TiO_2$ materials like carbon-doped titanium dioxide ($C—TiO_2$), ZnO (https://www.hindawi.com/journals/ijp/2013/795060/) or Nanocomposite coating of TiO2 and Polytetrafluoroethylene (http://onlinelibrary.wiley.com/doi/10.100²/adma.201201037/abstract) could be used as photo catalytic material.

The light sources 16 are advantageously LEDs typically with the following properties:
Power/led: 0.06-1 W
Wavelength in following ranges: 300-420 nm

The invention claimed is:
1. An electrostatic filter construction comprising:
   a charging unit, which charges particles to be filtered into a first electric potential and which is arranged in the electrostatic filter construction in a path of an air flow before filter elements,
   electrically conducting electrodes connected to a second electric potential different to the first electric potential of the charged particles and set substantially parallel to the path of the air flow, wherein the filter elements are positioned after the charging unit in the path of the air flow, and wherein filter each filter element has at least one designated UV-light source and an element of photo catalytic material.

2. The electrostatic filter construction according to claim 1, wherein the electrostatic filter construction is positioned in air ducts or ventilation channels and the filter elements are bag shaped.

3. The electrostatic filter construction according to claim 1, wherein bag shaped filter elements are positioned around the electrodes, and inside the bag shaped filter elements are positioned UV-light sources and photo catalytic material which is $TiO_2$.

4. The electrostatic filter construction according claim 2 wherein the at least one designated UV-light source and the element of photo catalytic material are positioned in front of the bag shaped filter element in the path of the air flow.

5. The electrostatic filter construction according to claim 1 wherein the electrically conducting electrodes are covered with photo catalytic material $TiO_2$ or an equivalent photo catalytic material and connected electrically to ground potential or to opposite polarity than high voltage unit for corona discharge before the electrically conducting electrodes.

6. The electrostatic filter construction according to claim 1, wherein the charging unit comprises corona strips including brush like extensions directed against the air flow.

7. The electrostatic filter construction according to claim 6, wherein the corona strips are connected to negative high voltage.

8. The electrostatic filter construction according to claim 2, wherein the bag shaped filter elements comprise a layer of particle filter media and of gas filter media.

9. The electrostatic filter construction according to claim 2, wherein the bag shaped filter elements comprise multiple subfilters.

10. The electrostatic filter construction according to claim 2, wherein the bag shaped filter elements are disposable.

11. The electrostatic filter construction according to claim 2, wherein inside the bag shaped filter elements are electrodes connected to a voltage, said voltage having a polarity which is opposite to the voltage of the charging unit.

12. The electrostatic filter construction according to claim 2, wherein the bag shaped filter elements are made of electrically conducting material.

13. The electrostatic filter construction according to claim 2, wherein one side of the bag shaped filter elements is covered with $TiO_2$ and this side is exposed to UV-light.

14. The electrostatic filter construction according to claim 1, wherein the electrostatic filter construction is connected to a mobile communication device.

15. The electrostatic filter construction according to claim 14, wherein the electrostatic filter construction is an integral part of the mobile communication device.

16. An air cleaning method, where an air flow is created and which method comprises the steps of:
    in a charging unit, charging the particles to be filtered into a first electric potential before the particles enter filter elements,
    attracting the charged particles by electrically conducting electrodes connected to a second electric potential different from the potential of the charged particles and set substantially parallel to a path of the airflow,
    guiding the charged air through filter elements positioned after the charging unit in the path of the air flow, and
    directing UV-light in or close to each bag shaped filter element and placing photo catalytic material close to the UV-light.

17. The air cleaning method according to claim 16, wherein the filter elements are bag shaped.

18. The air cleaning method according to claim 17, further comprising positioning the bag shaped filter elements around the electrically conducting electrodes, and positioning inside the bag shaped filter; UV-light sources and photo catalytic material elements which are $TiO_2$.

19. The air cleaning method according to claim 16, further comprising positioning at least one designated UV-light source and an element of photo catalytic material in front of the bag shaped filter element in the direction of the air flow.

20. The air cleaning method according to claim 16, further comprising covering the electrically conducting electrodes with photo catalytic material $TiO_2$ or an equivalent photo catalytic material and connecting electrically conducting electrodes electrically to ground potential.

21. The air cleaning method according to claim 16, wherein the charging unit comprises corona strips including brush like extensions directed against the air flow.

22. The air cleaning method according to claim 21, wherein the corona strips are connected to negative high voltage.

23. The air cleaning method according to claim 17, wherein the bag shaped filter elements comprise a layer of particle filter media and a layer of gas filter media.

24. The air cleaning method according to claim 17, wherein the bag shaped filter elements comprise multiple subfilters.

25. The air cleaning method according to claim 17, wherein the bag shaped filter elements are disposable.

26. The air cleaning method according to claim 16, wherein inside the bag shaped filter elements are electrodes connected to a voltage opposite to the voltage of the charging unit.

27. The air cleaning method according to claim 17, wherein the bag shaped filter elements are made of electrically conducting material.

28. The air cleaning method according to claim 17, wherein one side of the bag shaped filter elements is covered with $TiO_2$ and this side is exposed to UV-light.

29. The air cleaning method according to claim 16, wherein the electrostatic filter construction is connected to a mobile communication device.

30. The air cleaning method according to claim 29, wherein the electrostatic filter construction is an integral part of the mobile communication device.

31. A mobile filter unit comprising:
    a mobile communication device, and
    a filter unit connected to the mobile communication device, wherein the filter unit comprises:
    an air inlet,
    a fan for generating an air flow from behind of the mobile communication device,
    a high voltage unit for charging the air flow and particles in the air flow,
    TiO2-covered electrodes in the air flow connected to opposite polarity than the high voltage unit,
    UV-LEDs illuminating the TiO2-covered electrodes, and
    an outlet for the air flow directed towards of a user of the mobile communication device.

32. The mobile filter unit according to claim 31, wherein the electrodes are as filter consumable filter unit and the TiO2-covered electrodes are from aluminium, plastic or other suitable conductive materials and are forming a low pressure drop from.

33. The mobile filter unit according to claim 31, wherein the mobile filter unit includes a removable particle filter.

* * * * *